United States Patent
Franceschetti et al.

(10) Patent No.: US 9,186,479 B1
(45) Date of Patent: Nov. 17, 2015

(54) METHODS AND SYSTEMS FOR GATHERING HUMAN BIOLOGICAL SIGNALS AND CONTROLLING A BED DEVICE

(71) Applicant: Morphy Inc., San Francisco, CA (US)

(72) Inventors: Matteo Franceschetti, San Francisco, CA (US); Massimo Andreasi Bassi, San Francisco, CA (US)

(73) Assignee: MORPHY INC., San Francisco, CA (US)

( * ) Notice: Subject to any disclaimer, the term of this patent is extended or adjusted under 35 U.S.C. 154(b) by 0 days.

(21) Appl. No.: 14/732,608

(22) Filed: Jun. 5, 2015

Related U.S. Application Data

(60) Provisional application No. 62/008,480, filed on Jun. 5, 2014, provisional application No. 62/024,945, filed on Jul. 15, 2014, provisional application No. 62/159,177, filed on May 8, 2015, provisional application No. 62/161,142, filed on May 13, 2015.

(51) Int. Cl.
*A61M 21/02* (2006.01)
*A61M 21/00* (2006.01)

(52) U.S. Cl.
CPC ....... *A61M 21/02* (2013.01); *A61M 2021/0066* (2013.01); *A61M 2205/0294* (2013.01); *A61M 2205/3303* (2013.01); *A61M 2205/3306* (2013.01); *A61M 2205/3368* (2013.01); *A61M 2205/3375* (2013.01); *A61M 2205/3673* (2013.01); *A61M 2205/50* (2013.01); *A61M 2230/06* (2013.01); *A61M 2230/42* (2013.01); *A61M 2230/50* (2013.01); *A61M 2230/63* (2013.01)

(58) Field of Classification Search
CPC ................ A61M 16/00; A61M 21/02; A61M 2205/3306; A61M 2205/3368; A61M 2205/3375; A61M 2230/06; A61M 2230/10; A61M 2230/14; A61M 2230/42; A61M 2230/50; A61M 2230/63
USPC .................................. 600/26–28; 5/421, 422
See application file for complete search history.

(56) References Cited

U.S. PATENT DOCUMENTS

| | | | |
|---|---|---|---|
| 5,307,051 A | 4/1994 | Sedlmayr | |
| 5,353,788 A * | 10/1994 | Miles | A61M 16/00 128/204.21 |
| 5,479,939 A | 1/1996 | Ogino | |
| 5,902,255 A | 5/1999 | Ogino | |
| 5,948,303 A * | 9/1999 | Larson | G05D 23/1905 126/205 |
| 6,254,545 B1 | 7/2001 | Stasz et al. | |
| 6,765,489 B1 | 7/2004 | Ketelhohn et al. | |
| 6,774,795 B2 | 8/2004 | Eshelman et al. | |
| 6,784,826 B2 | 8/2004 | Kane et al. | |
| 6,825,769 B2 | 11/2004 | Colmenarez et al. | |
| 6,888,453 B2 | 5/2005 | Lutz et al. | |
| 6,890,304 B1 | 5/2005 | Uebaba et al. | |
| 7,089,099 B2 | 8/2006 | Shostak et al. | |
| 7,202,791 B2 | 4/2007 | Trajkovic | |
| 7,289,036 B2 | 10/2007 | Salzhauer et al. | |
| 7,369,680 B2 | 5/2008 | Strubbe et al. | |
| 7,372,370 B2 | 5/2008 | Stults et al. | |
| 7,734,334 B2 | 6/2010 | Mietus et al. | |
| 7,825,813 B2 | 11/2010 | Farhan et al. | |

(Continued)

*Primary Examiner* — Samuel Gilbert
(74) *Attorney, Agent, or Firm* — Perkins Coie LLP

(57) ABSTRACT

Introduced are methods and systems for an adjustable bed device configured to: gather biological signals associated with multiple users, such as heart rate, breathing rate, or temperature; analyze the gathered human biological signals; and heat or cool a bed based on the analysis.

3 Claims, 22 Drawing Sheets

(56) References Cited

U.S. PATENT DOCUMENTS

| | | | |
|---|---|---|---|
| 7,868,757 B2 | 1/2011 | Radivojevic et al. | |
| 7,883,480 B2 | 2/2011 | Dunlop et al. | |
| 8,035,508 B2 | 10/2011 | Breed et al. | |
| 8,292,819 B2 | 10/2012 | Kuo et al. | |
| 8,337,431 B2 | 12/2012 | Heruth et al. | |
| 8,348,840 B2 | 1/2013 | Heit et al. | |
| 8,355,769 B2 | 1/2013 | Popovic et al. | |
| 8,410,943 B2 | 4/2013 | Metz et al. | |
| 8,427,311 B2 | 4/2013 | Schlangen et al. | |
| 8,444,558 B2 | 5/2013 | Young et al. | |
| 8,461,996 B2 | 6/2013 | Gallagher et al. | |
| 8,493,220 B2 | 7/2013 | Virtanen et al. | |
| 8,512,221 B2 | 8/2013 | Kaplan et al. | |
| 8,523,758 B1 * | 9/2013 | Kirby | A61M 21/02 600/26 |
| 8,525,680 B2 | 9/2013 | Ribble et al. | |
| 8,628,462 B2 | 1/2014 | Berka et al. | |
| 8,628,478 B2 | 1/2014 | Wolfe et al. | |
| 8,641,616 B2 | 2/2014 | Shirai et al. | |
| 8,672,853 B2 | 3/2014 | Young et al. | |
| 8,692,677 B2 | 4/2014 | Wada et al. | |
| 8,698,635 B2 | 4/2014 | Epperson et al. | |
| 8,755,879 B2 | 6/2014 | Hang et al. | |
| 8,766,805 B2 | 7/2014 | Alameh et al. | |
| 8,803,366 B2 | 8/2014 | Proud | |
| 8,803,682 B2 | 8/2014 | Wong et al. | |
| 8,810,430 B2 | 8/2014 | Proud | |
| 8,836,516 B2 | 9/2014 | Wolfe et al. | |
| 8,850,421 B2 | 9/2014 | Proud | |
| 8,852,127 B2 | 10/2014 | Bell et al. | |
| 8,866,621 B2 | 10/2014 | Wolfe et al. | |
| 8,876,737 B2 | 11/2014 | Prendergast et al. | |
| 8,880,137 B2 | 11/2014 | Tomasco et al. | |
| 8,880,207 B2 | 11/2014 | Karunajeewa et al. | |
| 8,932,199 B2 | 1/2015 | Popovic et al. | |
| 8,933,809 B2 | 1/2015 | Emori et al. | |
| 8,939,884 B2 | 1/2015 | Kashima et al. | |
| 8,948,861 B2 | 2/2015 | Kalik et al. | |
| 8,961,413 B2 | 2/2015 | Liden et al. | |
| 8,979,730 B2 | 3/2015 | Rademaker et al. | |
| 8,988,014 B2 | 3/2015 | Noguchi et al. | |
| 9,000,931 B2 | 4/2015 | Tomimori et al. | |
| 9,011,347 B2 | 4/2015 | Addison et al. | |
| 2002/0128700 A1 * | 9/2002 | Cross, Jr. | A61N 1/0529 607/117 |
| 2011/0115635 A1 * | 5/2011 | Petrovski | A47C 21/048 340/584 |
| 2012/0143095 A1 * | 6/2012 | Nakamura | G01C 22/006 600/595 |

* cited by examiner

METHODS AND SYSTEMS FOR GATHERING HUMAN BIOLOGICAL SIGNALS AND CONTROLLING A BED DEVICE

CROSS-REFERENCE TO RELATED APPLICATIONS

This application claims priority to the following U.S. provisional patent applications: U.S. provisional patent application Ser. No. 62/008,480, filed Jun. 5, 2014; U.S. provisional patent application Ser. No. 62/024,945, filed Jul. 15, 2014; U.S. provisional patent application Ser. No. 62/159,177, filed May 8, 2015; and U.S. provisional patent application Ser. No. 62/161,142, filed May 13, 2015; which applications are incorporated herein in their entirety and by this reference thereto.

TECHNICAL FIELD

Various embodiments relate generally to home automation devices, and human biological signal gathering and analysis.

BACKGROUND

According to current scientific research into sleep, there are two major stages of sleep: rapid eye movement ("REM") sleep, and non-REM sleep. First comes non-REM sleep, followed by a shorter period of REM sleep, and then the cycle starts over again.

There are three stages of non-REM sleep. Each stage can last from 5 to 15 minutes. A person goes through all three stages before reaching REM sleep.

In stage one, a person's eyes are closed, but the person is easily woken up. This stage may last for 5 to 10 minutes.

In stage two, a person is in light sleep. A person's heart rate slows and the person's body temperature drops. The person's body is getting ready for deep sleep.

Stage three is the deep sleep stage. A person is harder to rouse during this stage, and if the person was woken up, the person would feel disoriented for a few minutes. During the deep stages of non-REM sleep, the body repairs and regrows tissues, builds bone and muscle, and strengthens the immune system.

REM sleep happens 90 minutes after a person falls asleep. Dreams typically happen during REM sleep. The first period of REM typically lasts 10 minutes. Each of later REM stages gets longer, and the final one may last up to an hour. A person's heart rate and breathing quickens. A person can have intense dreams during REM sleep, since the brain is more active. REM sleep affects learning of certain mental skills.

Even in today's technological age, supporting healthy sleep is relegated to the technology of the past such as an electric blanket, a heated pad, or a bed warmer. The most advanced of these technologies, an electric blanket, is a blanket with an integrated electrical heating device which can be placed above the top bed sheet or below the bottom bed sheet. The electric blanket may be used to pre-heat the bed before use or to keep the occupant warm while in bed. However, turning on the electric blanket requires the user to remember to manually turn on the blanket, and then manually turn it on. Further, the electric blanket provides no additional functionality besides warming the bed.

SUMMARY

Introduced are methods and systems for an adjustable bed device configured to: gather biological signals associated with multiple users, such as heart rate, breathing rate, or temperature; analyze the gathered human biological signals; and heat or cool a bed based on the analysis.

In one embodiment, one or more user sensors, associated with a piece of furniture, such as a bed, measure the bio signals associated with a user, such as the heart rate associated with said user or breathing rate associated with said user. One or more environment sensors measure the environment property such as temperature, humidity, light, or sound. Based on the bio signals associated with said user and environment properties received, the system determines the time at which to send an instruction to an appliance to turn on or to turn off. In one embodiment, the appliance is a bed device, capable of heating or cooling the user's bed. In another embodiment, the appliance is a thermostat, a light, a coffee machine, or a humidifier.

In another embodiment, based on the heart rate, temperature, and breathing rate, associated with a user, the system determines the sleep phase associated with said user. Based on the sleep phase and the user-specified wake-up time, the system determines a time to wake up the user, so that the user does not feel tired or disoriented when woken up.

BRIEF DESCRIPTION OF THE DRAWINGS

These and other objects, features and characteristics of the present embodiments will become more apparent to those skilled in the art from a study of the following detailed description in conjunction with the appended claims and drawings, all of which form a part of this specification. While the accompanying drawings include illustrations of various embodiments, the drawings are not intended to limit the claimed subject matter.

DETAILED DESCRIPTION

Figure 1:
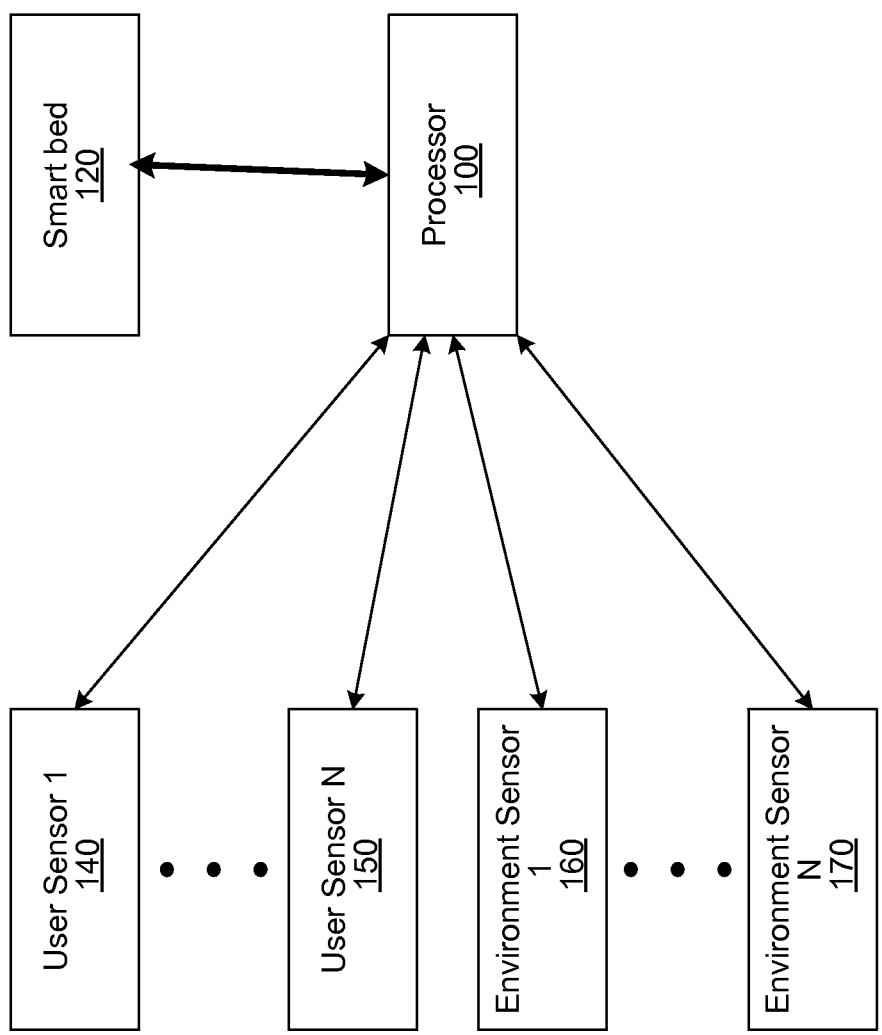
FIG. 1 is a diagram of a bed device, according to one embodiment.

Examples of a method, apparatus, and computer program for automating the control of home appliances and improving the sleep environment are disclosed below. In the following description, for the purposes of explanation, numerous specific details are set forth in order to provide a thorough understanding of the embodiments of the invention. One skilled in the art will recognize that the embodiments of the invention may be practiced without these specific details or with an equivalent arrangement. In other instances, well-known structures and devices are shown in block diagram form in order to avoid unnecessarily obscuring the embodiments of the invention.

TERMINOLOGY

Brief definitions of terms, abbreviations, and phrases used throughout this application are given below.

In this specification, the term "biological signal" and "bio signal" are synonyms, and are used interchangeably.

Reference in this specification to "sleep phase" means light sleep, deep sleep, or REM sleep. Light sleep comprises stage one and stage two, non-REM sleep.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described that may be exhibited by some embodiments and not by others. Similarly, various requirements are described that may be requirements for some embodiments but not others.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements. The coupling or connection between the elements can be physical, logical, or a combination thereof. For example, two devices may be coupled directly, or via one or more intermediary channels or devices. As another example, devices may be coupled in such a way that information can be passed there between, while not sharing any physical connection with one another. Additionally, the words "herein," "above," "below," and words of similar import, when used in this application, shall refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

If the specification states a component or feature "may," "can," "could," or "might" be included or have a characteristic, that particular component or feature is not required to be included or have the characteristic.

The term "module" refers broadly to software, hardware, or firmware components (or any combination thereof). Modules are typically functional components that can generate useful data or another output using specified input(s). A module may or may not be self-contained. An application program (also called an "application") may include one or more modules, or a module may include one or more application programs.

The terminology used in the Detailed Description is intended to be interpreted in its broadest reasonable manner, even though it is being used in conjunction with certain examples. The terms used in this specification generally have their ordinary meanings in the art, within the context of the disclosure, and in the specific context where each term is used. For convenience, certain terms may be highlighted, for example using capitalization, italics, and/or quotation marks. The use of highlighting has no influence on the scope and meaning of a term; the scope and meaning of a term is the same, in the same context, whether or not it is highlighted. It will be appreciated that the same element can be described in more than one way.

Consequently, alternative language and synonyms may be used for any one or more of the terms discussed herein, but special significance is not to be placed upon whether or not a term is elaborated or discussed herein. A recital of one or more synonyms does not exclude the use of other synonyms. The use of examples anywhere in this specification, including examples of any terms discussed herein, is illustrative only and is not intended to further limit the scope and meaning of the disclosure or of any exemplified term. Likewise, the disclosure is not limited to various embodiments given in this specification.

Bed Device

FIG. 1 is a diagram of a bed device, according to one embodiment. Any number of user sensors 140, 150 monitor the bio signals associated with a user, such as the heart rate, the breathing rate, the temperature, motion, or presence, associated with said user. Any number of environment sensors 160, 170 monitor environment properties, such as temperature, sound, light, or humidity. The user sensors 140, 150 and the environment sensors 160, 170 communicate their measurements to the processor 100. The environment sensors 160, 170, measure the properties of the environment that the environment sensors 160, 170 are associated with. In one embodiment, the environment sensors 160, 170 are placed next to the bed. The processor 100 determines, based on the bio signals associated with said user, historical bio signals associated with said user, user-specified preferences, exercise data associated with said user, or the environment properties received, a control signal, and a time to send said control signal to a bed device 120.

Figure 2:
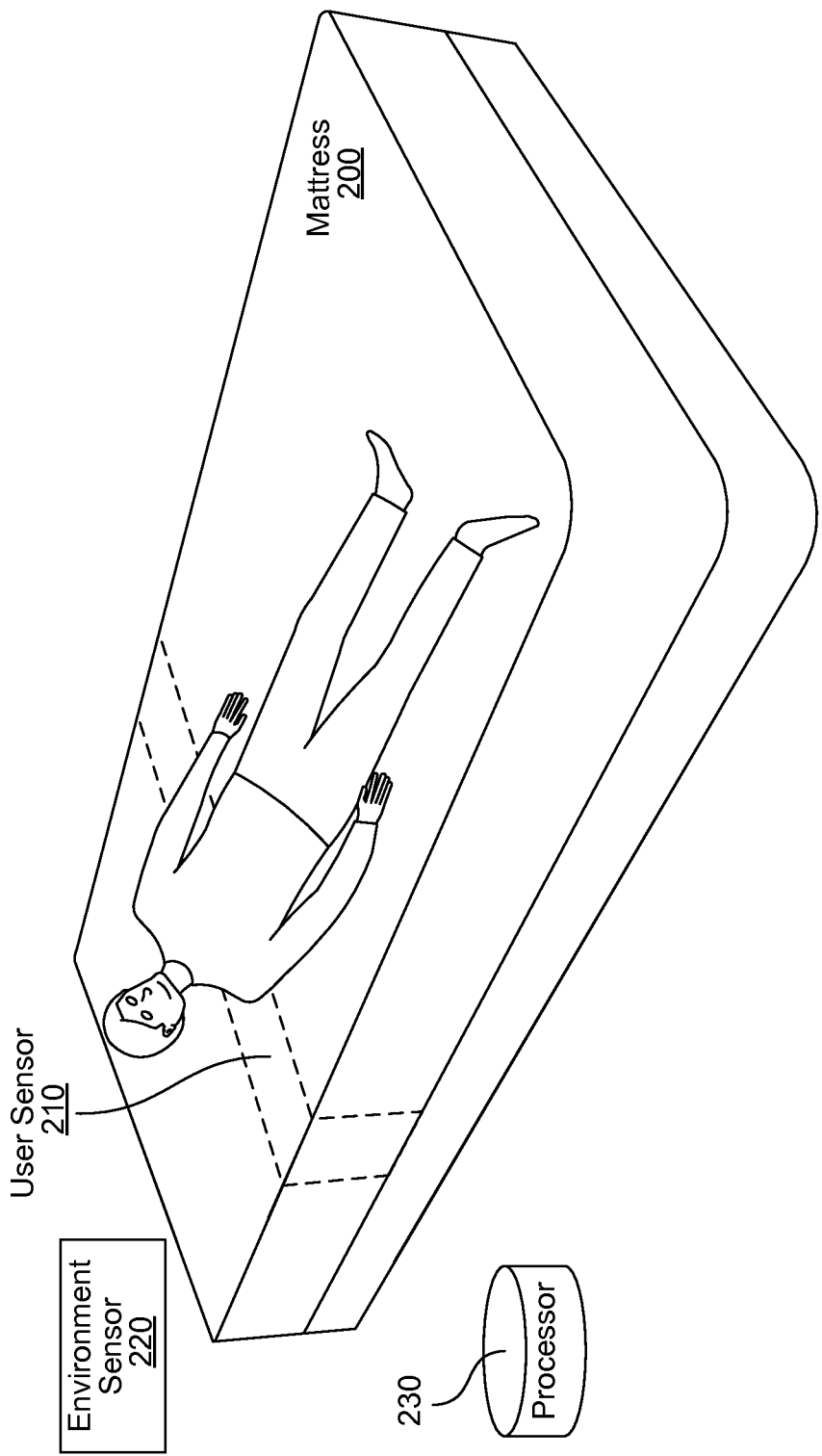
FIG. 2 illustrates an example of a bed device, according to one embodiment.

FIG. 2 illustrates an example of the bed device of FIG. 1, according to one embodiment. A user sensor 210, associated with a mattress 200 of the bed device 120, monitors bio signals associated with a user sleeping on the mattress 200. The user sensor 210 can be built into the mattress 200, or can be part of a bed pad device. Alternatively, the user sensor 210 can be a part of any other piece of furniture, such as a rocking chair, a couch, an armchair etc. The user sensor 210 comprises a temperature sensor, or a piezo sensor. The environment sensor 220 measures environment properties such as temperature, sound, light or humidity. According to one embodiment, the environment sensor 220 is associated with the environment surrounding the mattress 200. The user sensor 210 and the environment sensor 220 communicate the measured environment properties to the processor 230. In some embodiments, the processor 230 can be similar to the processor 100 of FIG. 1 A processor 230 can be connected to the user sensor 210, or the environment sensor 220 by a computer bus, such as an I2C bus. Also, the processor 230 can be connected to the user sensor 210, or the environment sensor 220 by a communication network. By way of example, the communication network connecting the processor 230 to the user sensor 210, or the environment sensor 220 includes one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

The processor 230 is any type of microcontroller, or any processor in a mobile terminal, fixed terminal, or portable terminal including a mobile handset, station, unit, device, multimedia computer, multimedia tablet, Internet node, cloud computer, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, the accessories and peripherals of these devices, or any combination thereof.

Figure 3:
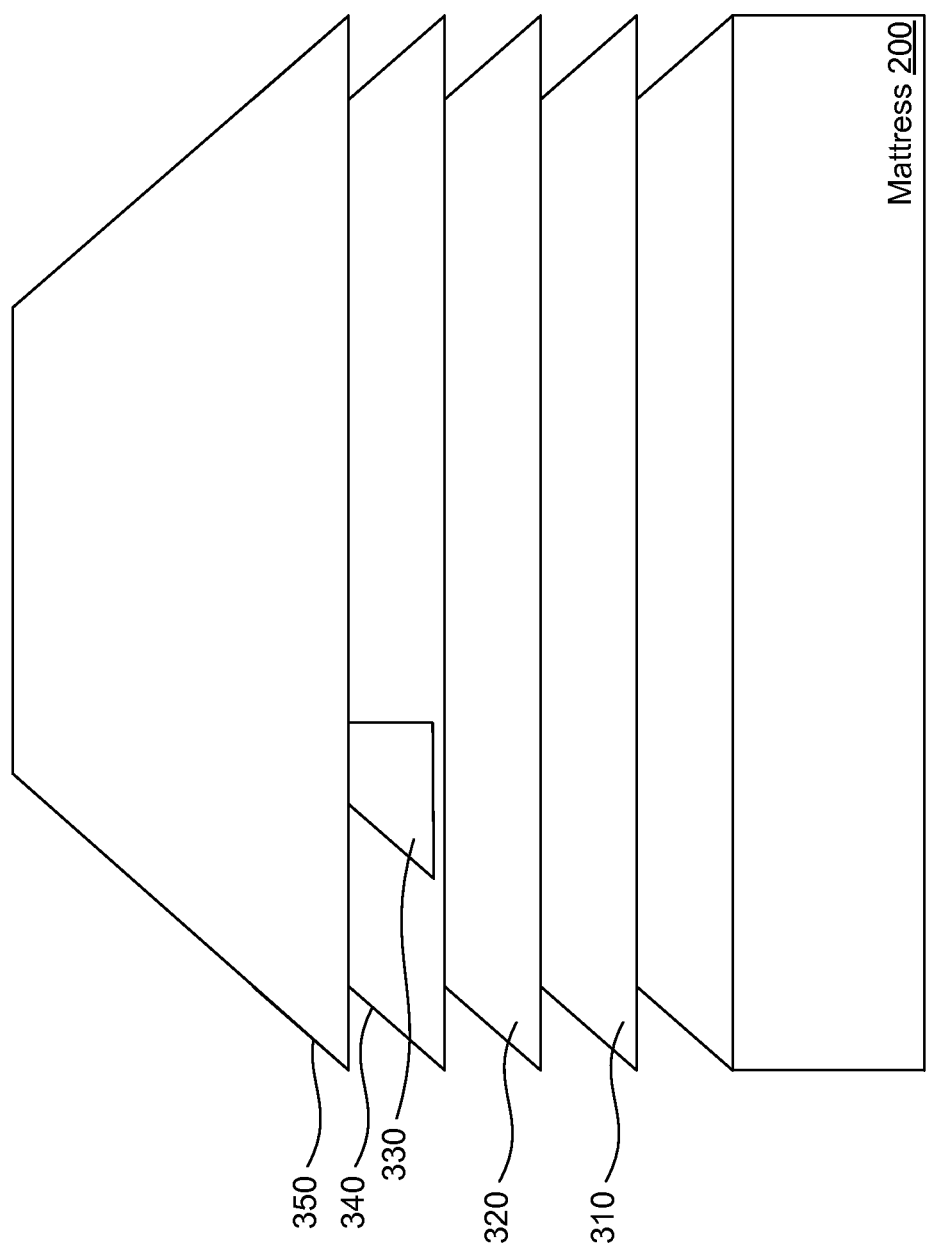
FIG. 3 illustrates an example of layers comprising a bed pad device, according to one embodiment.

FIG. 3 illustrates an example of layers comprising the bed pad device of FIG. 1, according to one embodiment. In some embodiments, the bed pad device 120 is a pad that can be placed on top of the mattress. Bed pad device 120 comprises a number of layers. A top layer 350 comprises fabric. A layer 340 comprises batting, and a sensor strip 330. A layer 320 comprises coils for cooling or heating the bed device. A layer 310 comprises waterproof material.

Figure 4:
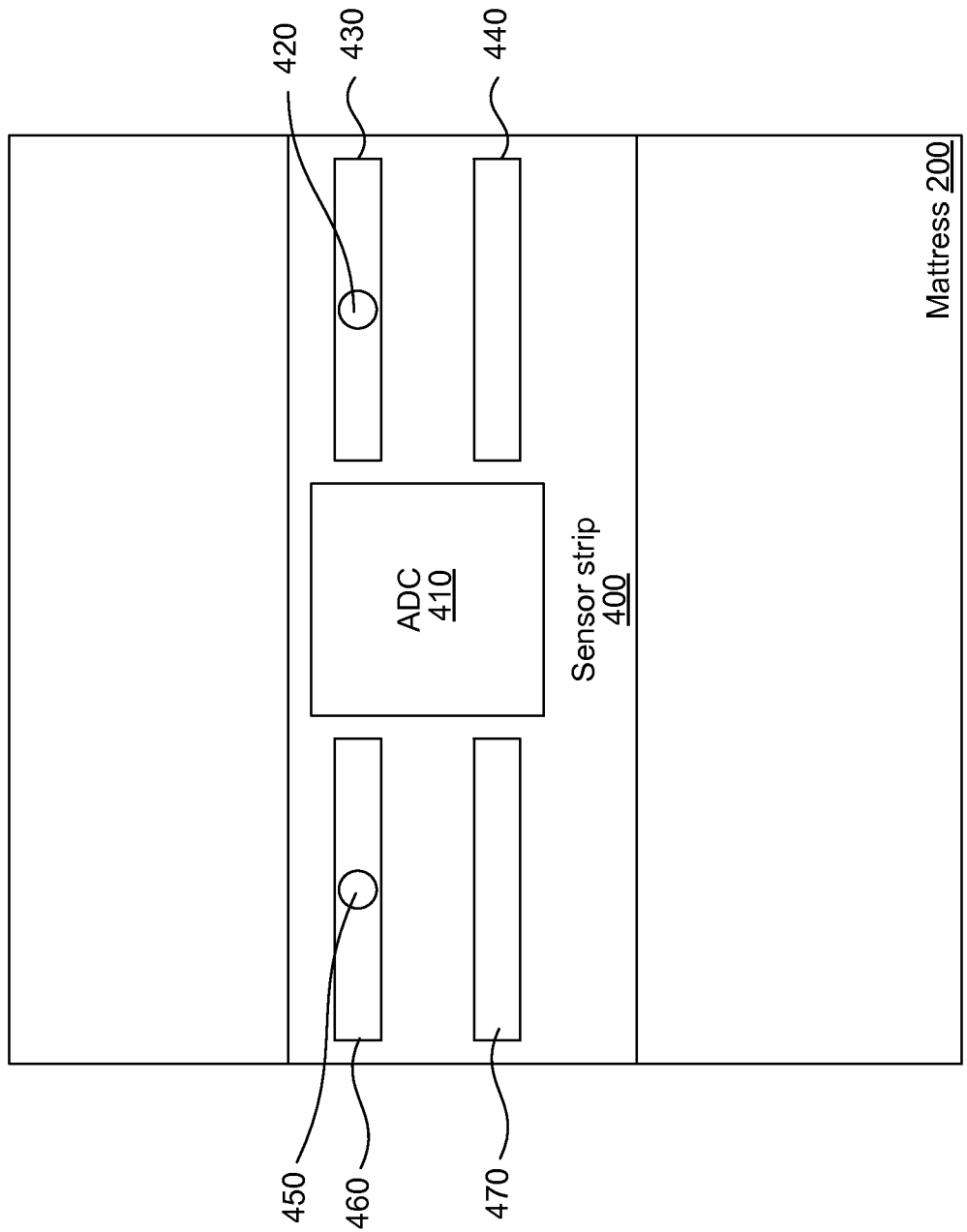
FIG. 4 illustrates a user sensor placed on a sensor strip, according to one embodiment.

FIG. 4 illustrates a user sensor 420, 440, 450, 470 placed on a sensor strip 400, according to one embodiment. In some embodiments, the user sensors 420, 440, 450, 470 can be similar to or part of the user sensor 210 of FIG. 2. Sensors 470 and 440 comprise a piezo sensor, which can measure a bio signal associated with a user, such as the heart rate and the breathing rate. Sensors 450 and 420 comprise a temperature sensor. According to one embodiment, sensors 450, and 470 measure the bio signals associated with one user, while sensors 420, 440 measure the bio signals associated with another user. Analog-to-digital converter 410 converts the analog sensor signals into digital signals to be communicated to a processor. Computer bus 430 and 460, such as the I2C bus, communicates the digitized bio signals to a processor.

Figure 5B:
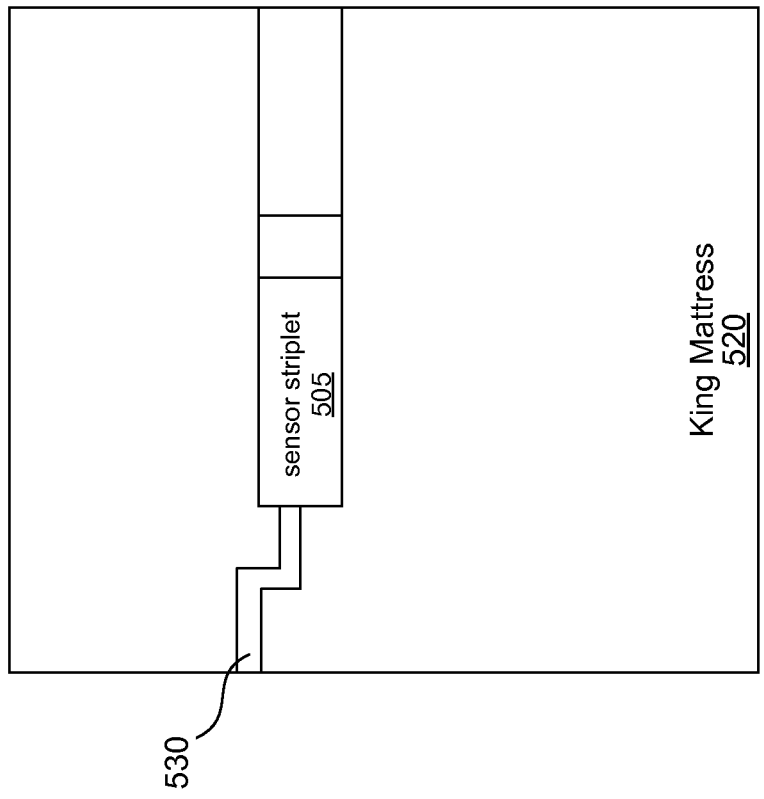
FIGS. 5A, 5B, 5C, and 5D show different configurations of a sensor strip, to fit different size mattresses, according to one embodiment.
Figure 5A:
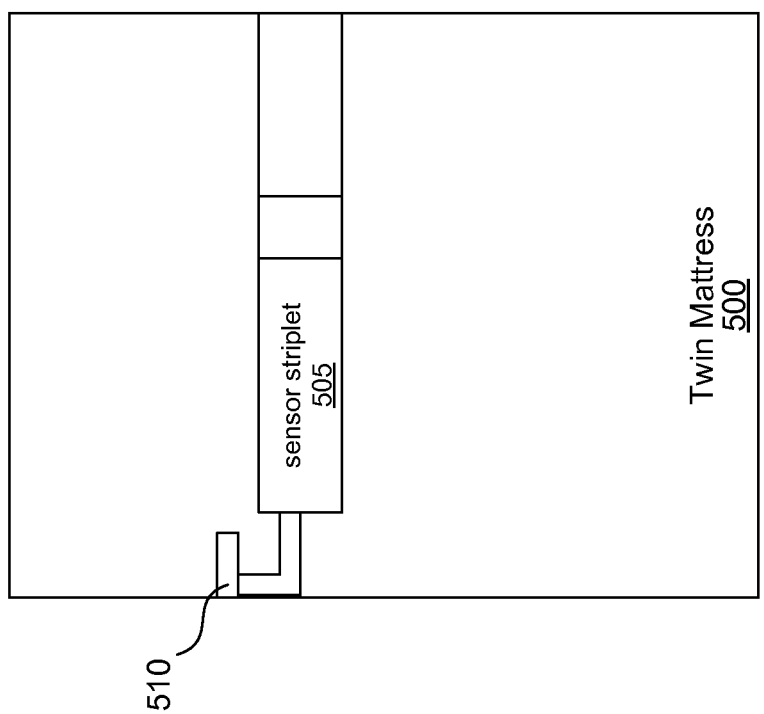
Figure 5C:
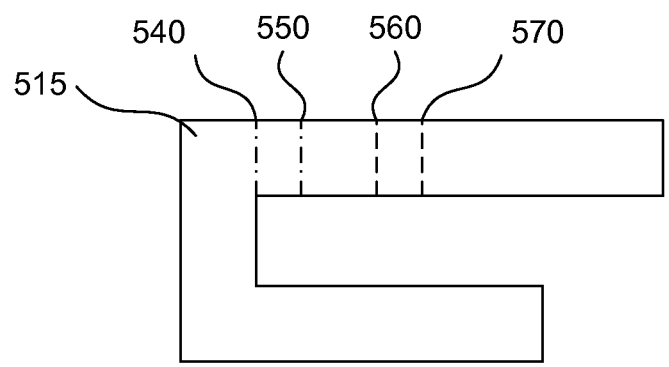
Figure 5D:
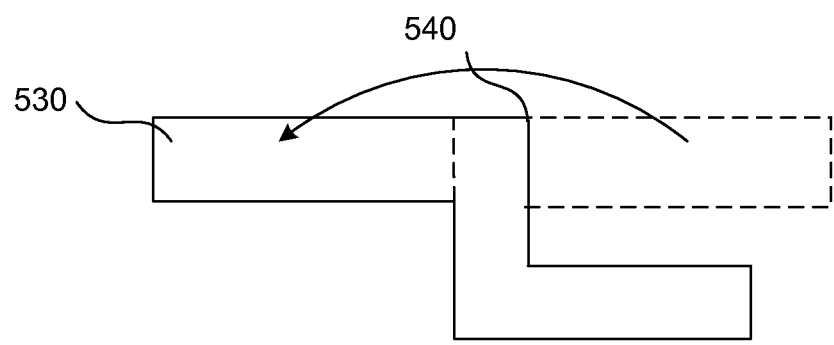

FIGS. 5A and 5B show different configurations of the sensor strip, to fit different size mattresses, according to one embodiment. FIGS. 5C and 5D show how such different configurations of the sensor strip can be achieved. Specifically, sensor strip 400 comprises a computer bus 510, 530, and a sensor striplet 505. The computer bus 510, 530 can be bent at predetermined locations 540, 550, 560, 570. Bending the computer bus 515 at location 540 produces the maximum total length of the computer bus 530. Computer bus 530 combined with a sensor striplet 505, fits a king size mattress 520. Bending the computer bus 515 at location 570 produces the smallest total length of the computer bus, 510. Computer bus 510 combined with a sensor striplet 505, fits a twin size mattress 500. Bending the computer bus 515 at location 560, enables the sensor strip 400 to fit a full-size bed. Bending the computer bus 515 at location 550 enables the sensor strip 400 to fit a queen-size bed. In some embodiments, twin mattress 500, or king mattress 520 can be similar to the mattress 200 of FIG. 2.

Figure 6A:
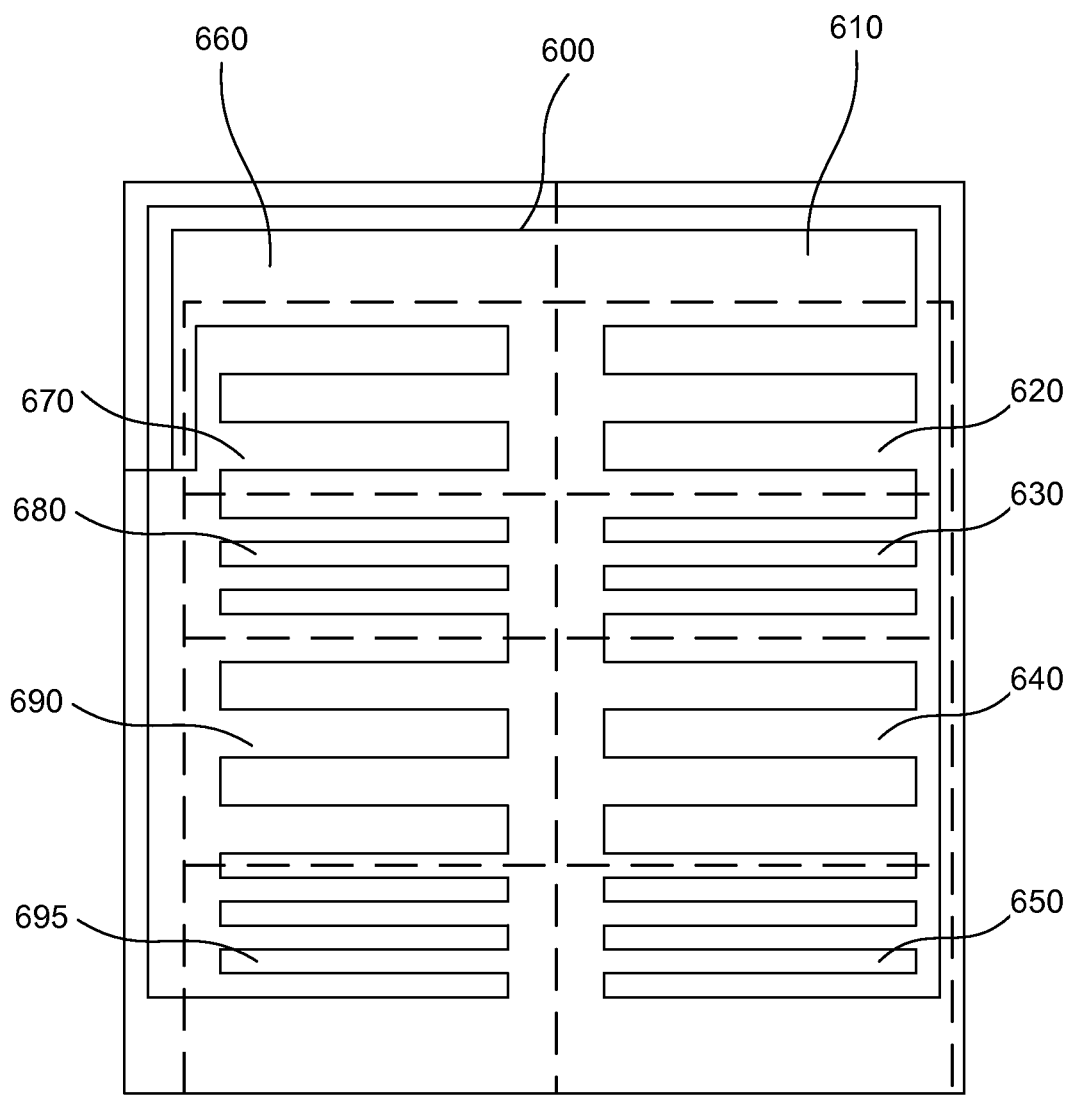
FIG. 6A illustrates the division of the heating coil into zones and subzones, according to one embodiment.

FIG. 6A illustrates the division of the heating coil 600 into zones and subzones, according to one embodiment. Specifically, the heating coil 600 is divided into two zones 660 and 610, each corresponding to one user of the bed. Each zone 660 and 610 can be heated or cooled independently of the other zone in response to the user's needs. To achieve independent heating of the two zones 660 and 610, the power supply associated with the heating coil 600 is divided into two zones, each power supply zone corresponding to a single user zone 660, 610. Further, each zone 660 and 610 is further subdivided into subzones. Zone 660 is divided into subzones 670, 680, 690, and 695. Zone 610 is divided into subzones 620, 630, 640, and 650. The distribution of coils in each subzone is configured so that the subzone is uniformly heated. However, the subzones may differ among themselves in the density of coils. For example, the data associated with said user subzone 670 has lower density of coils than subzone 680. This will result in subzone 670 having lower temperature than subzone 680, when the coils are heated. Similarly, when the coils are used for cooling, subzones 670 will have higher temperature than subzone 680. According to one embodiment, subzones 680 and 630 with highest coil density correspond to the user's lower back; and subzones 695 and 650 with highest coil density correspond to user's feet. According to one embodiment, even if the users switch sides of the bed, the system will correctly identify which user is sleeping in which zone by identifying the user based on any of the following signals alone, or in combination: heart rate, breathing rate, body motion, or body temperature associated with said user.

In another embodiment, the power supply associated with the heating coil 600 is divided into a plurality of zones, each power supply zone corresponding to a subzone 620, 630, 640, 650, 670, 680, 690, 695. The user can control the temperature of each subzone 620, 630, 640, 650, 670, 680, 690, 695 independently. Further, each user can independently specify the temperature preferences for each of the subzones. Even if the users switch sides of the bed, the system will correctly identify the user, and the preferences associated with the user by identifying the user based on any of the following signals alone, or in combination: heart rate, breathing rate, body motion, or body temperature associated with said user.

Figure 6B:
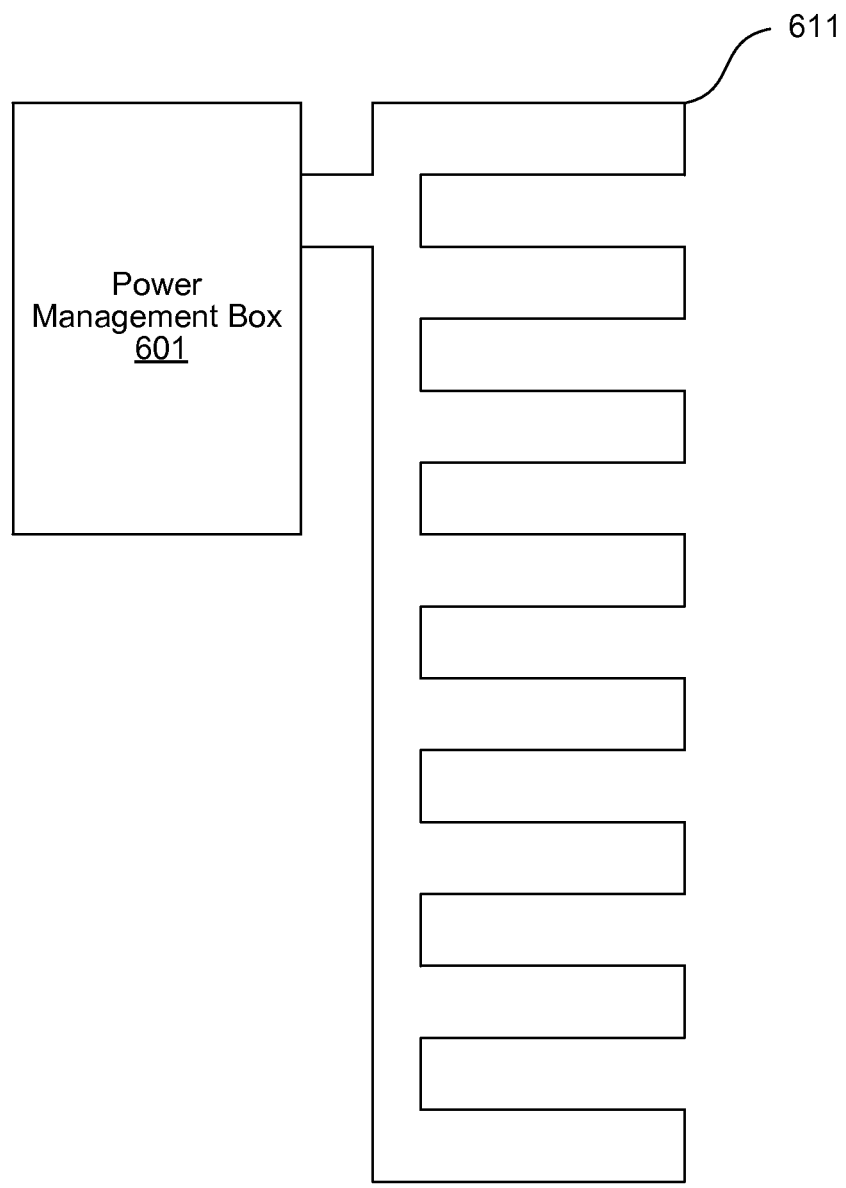
FIGS. 6B and 6C illustrate the independent control of the different subzones, according to one embodiment.
Figure 6C:
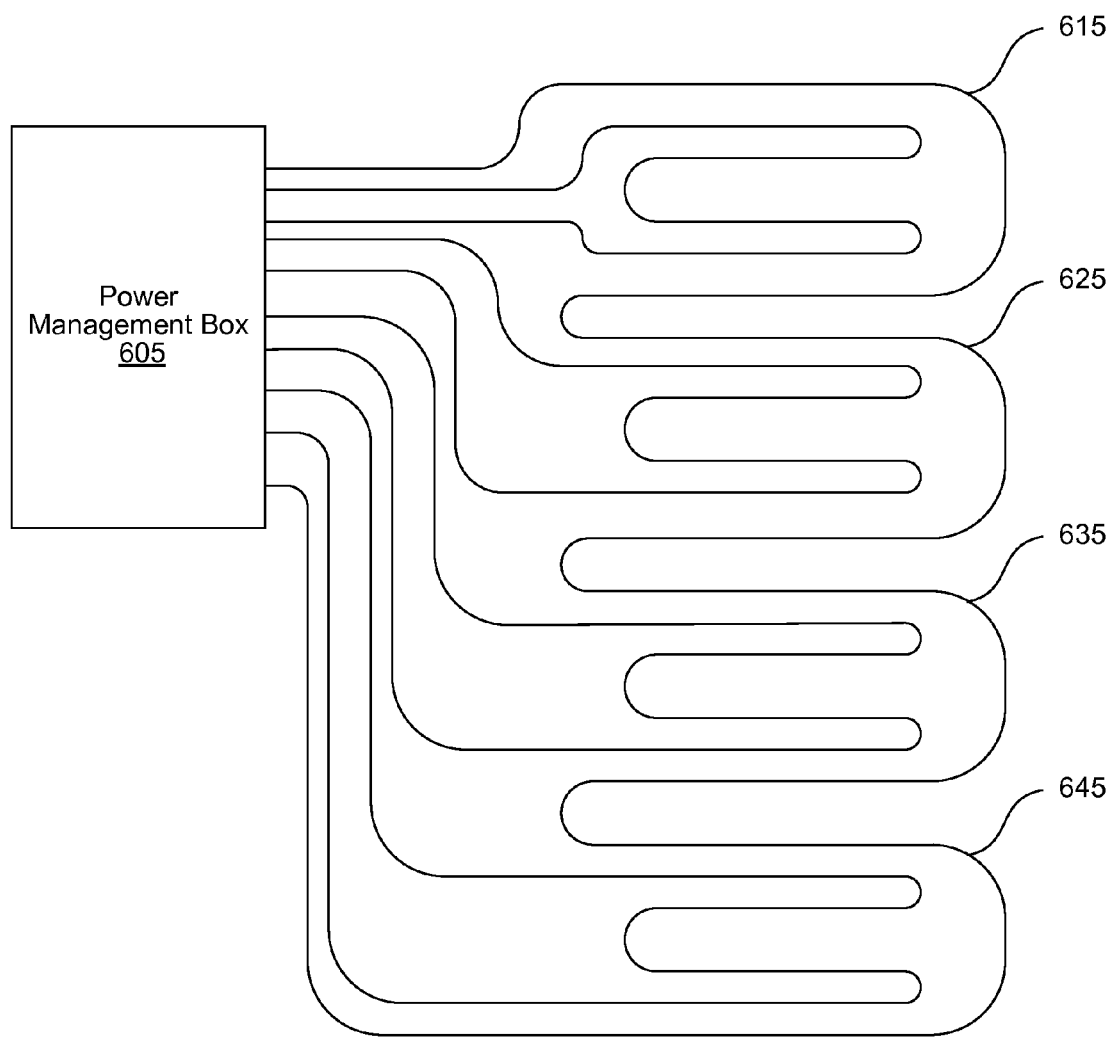

FIGS. 6B and 6C illustrate the independent control of the different subzones in each zone 610, 660, according to one embodiment. Set of uniform coils 611, connected to power management box 601, uniformly heats or cools the bed. Another set of coils, targeting specific areas of the body such as the neck, the back, the legs, or the feet, is layered on top of the uniform coils 611. Subzone 615 heats or cools the neck. Subzone 625 heats or cools the back. Subzone 635 heats or cools the legs, and subzone 645 heats or cools the feet. Power is distributed to the coils via duty cycling of the power supply 605. Contiguous sets of coils can be heated or cooled at different levels by assigning the power supply duty cycle to each set of coils. The user can control the temperature of each subzone independently.

Figure 7:
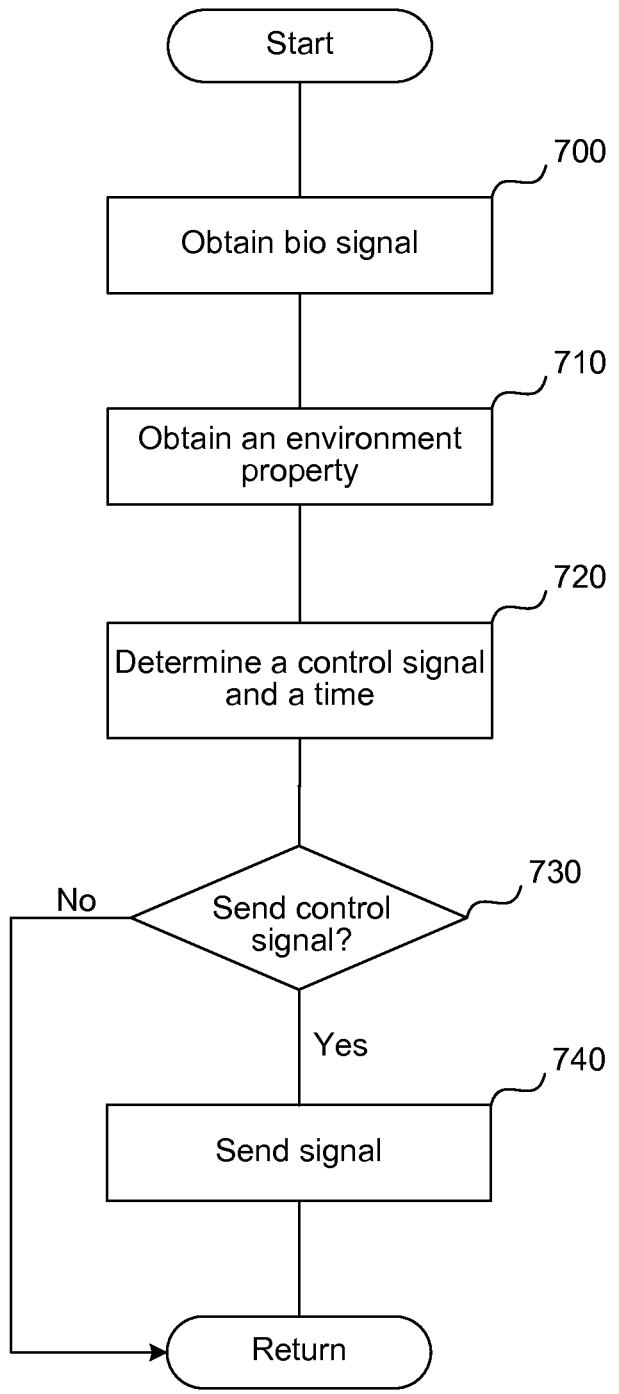
FIG. 7 is a flowchart of the process for deciding when to heat or cool the bed device, according to one embodiment.

FIG. 7 is a flowchart of the process for deciding when to heat or cool the bed device, according to one embodiment. At block 700, the process obtains a biological signal associated with a user, such as presence in bed, motion, breathing rate, heart rate, or a temperature. The process obtains said biological signal from a sensor associated with a user. Further, at block 710, the process obtains environment property, such as the amount of ambient light and the bed temperature. The process obtains environment property from an environment sensor associated with the bed device. If the user is in bed, the bed temperature is low, and the ambient light is low, the process sends a control signal to the bed device. The control signal comprises an instruction to heat the bed device to the average nightly temperature associated with said user. According to another embodiment, the control signal comprises an instruction to heat the bed device to a user-specified temperature. Similarly, if the user is in bed, the bed temperature is high, and the ambient light is low, the process sends a control signal to the bed device to cool the bed device to the average nightly temperature associated with said user. According to another embodiment, the control signal comprises an instruction to cool the bed device to a user-specified temperature.

In another embodiment, in addition to obtaining the biological signal associated with said user, and the environment property, the process obtains a history of biological signals associated with said user. The history of biological signals can be stored in a database associated with the bed device, or in a database associated with a user. The history of biological signals comprises the average bedtime the user went to sleep for each day of the week; that is, the history of biological signals comprises the average bedtime associated with said user on Monday, the average bedtime associated with said user on Tuesday, etc. For a given day of the week, the process determines the average bedtime associated with said user for that day of the week, and sends the control signal to the bed device, allowing enough time for the bed to reach the desired temperature, before the average bedtime associated with said user. The control signal comprises an instruction to heat, or cool the bed to a desired temperature. The desired temperature may be automatically determined, such as by averaging the historical nightly temperature associated with a user, or the desired temperature may be specified by the user.

Bio Signal Processing

The technology disclosed here categorizes the sleep phase associated with a user as light sleep, deep sleep, or REM sleep. Light sleep comprises stage one and stage two sleep. The technology performs the categorization based on the breathing rate associated with said user, heart rate associated with said user, motion associated with said user, and body temperature associated with said user. Generally, when said user is awake the breathing is erratic. When the user is sleeping, the breathing becomes regular. The transition between being awake and sleeping is quick, and lasts less than 1 minute.

Figure 8:
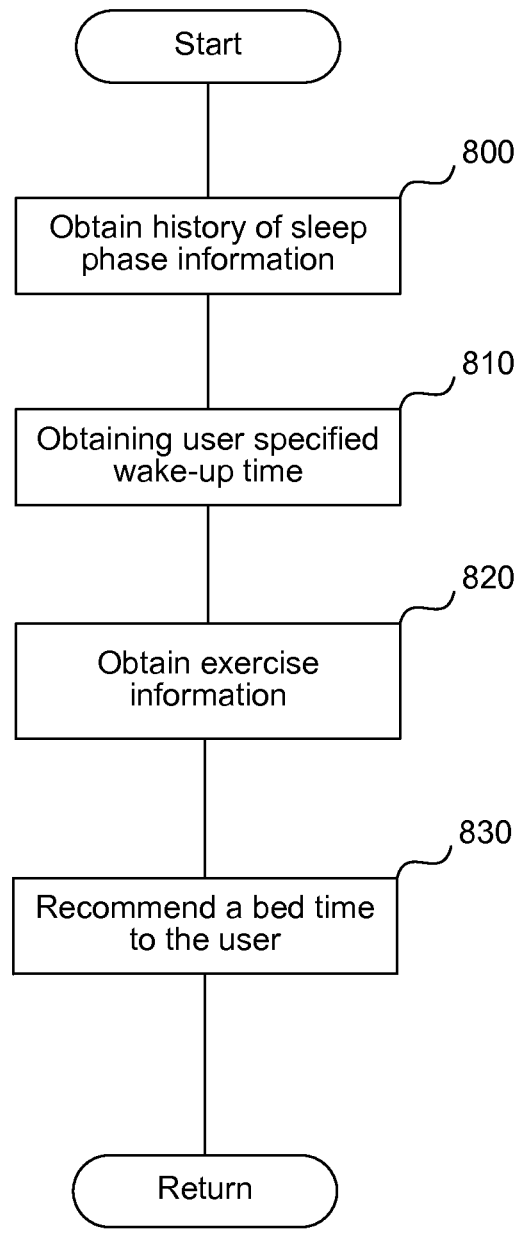
FIG. 8 is a flowchart of the process for recommending a bed time to a user, according to one embodiment.

FIG. 8 is a flowchart of the process for recommending a bed time to the user, according to one embodiment. At block 800, the process obtains a history of sleep phase information associated with said user. The history of sleep phase information comprises an amount of time the user spent in each of the sleep phases, light sleep, deep sleep, or REM sleep. The history of sleep phase information can be stored in a database associated with the user. Based on this information, the process determines how much light sleep, deep sleep, and REM sleep, the user needs on average every day. In another embodiment, the history of sleep phase information comprises the average bedtime associated with said user for each day of the week (e.g. the average bedtime associated with said user on Monday, the average bedtime associated with said user on Tuesday, etc.). At block 810, the process obtains user-specified wake-up time, such as the alarm setting associated with said user. At block 820, the process obtains exercise information associated with said user, such as the distance the user ran that day, the amount of time the user exercised in the gym, or the amount of calories the user burned that day. According to one embodiment, the process obtains said exercise information from a user phone, a wearable device, a fitbit bracelet, or a database storing said exercise information. Based on all this information, at block 830, the process recommends a bedtime to the user. For example, if the user has not been getting enough deep and REM sleep in the last few days, the process recommends an earlier bedtime to the user. Also, if the user has exercised more than the average daily exercise, the process recommends an earlier bedtime to the user.

Figure 9:
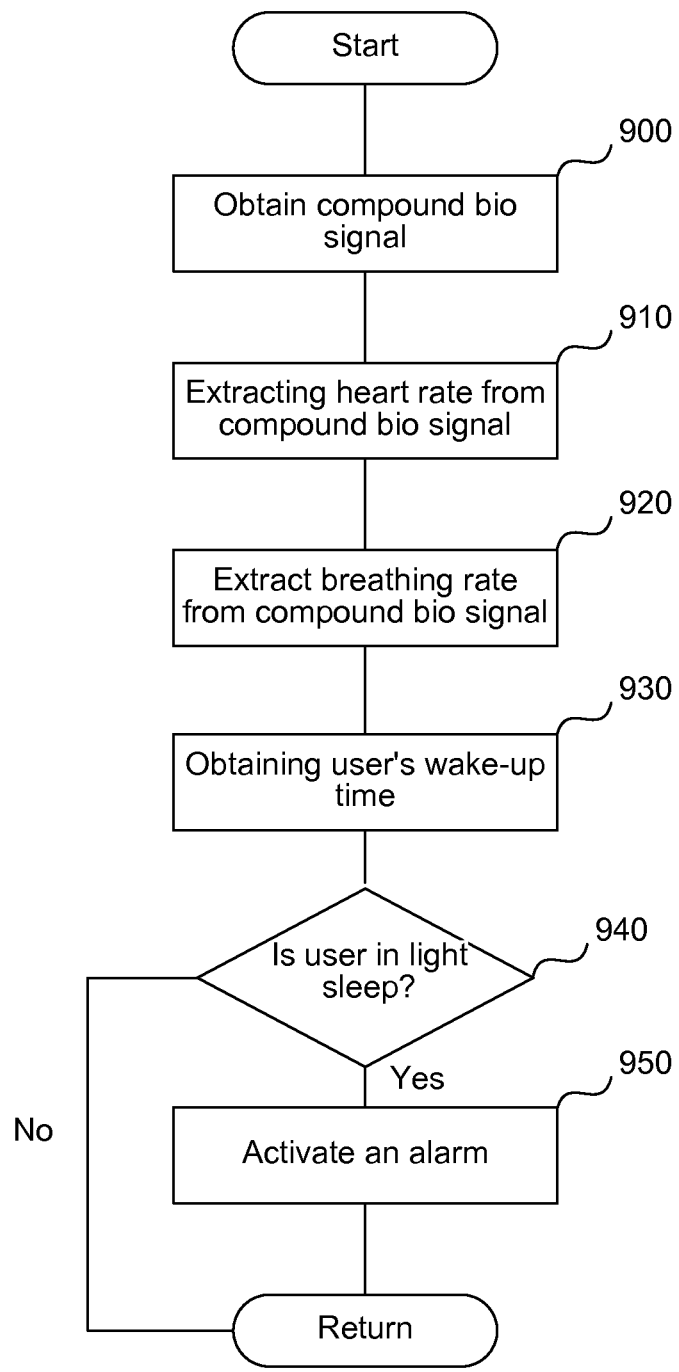
FIG. 9 is a flowchart of the process for activating the user's alarm, according to one embodiment.

FIG. 9 is a flowchart of the process for activating a user's alarm, according to one embodiment. At block 900, the process obtains the compound bio signal associated with said user. The compound bio signal associated with said user comprises the heart rate associated with said user, and the breathing rate associated with said user. According to one embodiment, the process obtains the compound bio signal from a sensor associated with said user. At block 910, the process extracts the heart rate signal from the compound bio signal. For example, the process extracts the heart rate signal associated with said user by performing low-pass filtering on the compound bio signal. Also, at block 920, the process extracts the breathing rate signal from the compound bio signal. For example, the process extracts the breathing rate by performing bandpass filtering on the compound bio signal. The breathing rate signal includes breath duration, pauses between breaths, as well as breaths per minute. At block 930, the process obtains user's wake-up time, such as the alarm setting associated with said user. Based on the heart rate signal and the breathing rate signal, the process determines the sleep phase associated with said user, and if the user is in light sleep, and current time is at most one hour before the alarm time, at block 940, the process activates an alarm. Waking up the user during the deep sleep or REM sleep is detrimental to the user's health because the user will feel disoriented, groggy, and will suffer from impaired memory. Consequently, at block 950, the process activates an alarm, when the user is in light sleep and when the current time is at most one hour before the user specified wake-up time.

Figure 10:
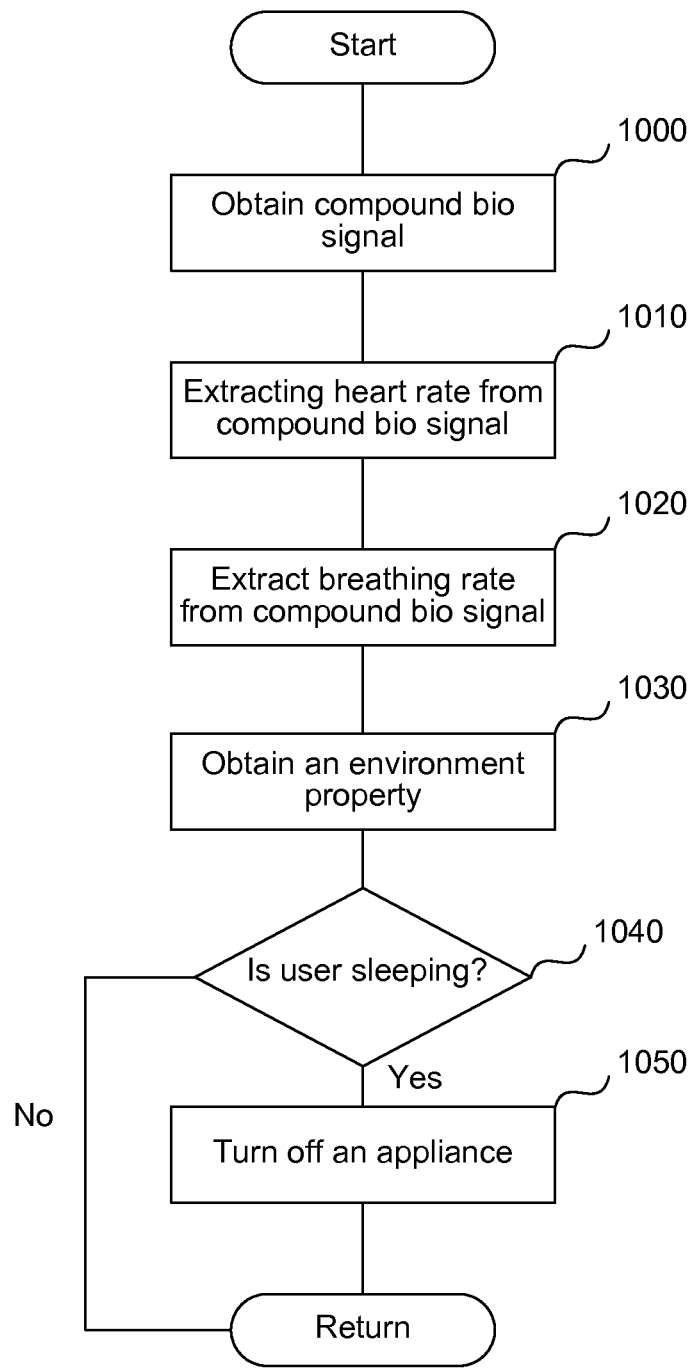
FIG. 10 is a flowchart of the process for turning off an appliance, according to one embodiment.

FIG. 10 is a flowchart of the process for turning off an appliance, according to one embodiment. At block 1000, the process obtains the compound bio signal associated with said user. The compound bio signal comprises the heart rate associated with said user, and the breathing rate associated with said user. According to one embodiment, the process obtains the compound bio signal from a sensor associated with said user. At block 1010, the process extracts the heart rate signal from the compound bio signal by, for example, performing low-pass filtering on the compound bio signal. Also, at block 1020, the process extracts the breathing rate signal from the compound bio signal by, for example, performing bandpass filtering on the compound bio signal. At block 1030, the process obtains an environment property, comprising temperature, humidity, light, sound from an environment sensor associated with said user sensor. Based on the environment property and the sleep state associated with said user, at block 1040, the process determines whether the user is sleeping. If the user is sleeping, the process, at block 1050, turns an appliance off. For example, if the user is asleep and the environment temperature is above the average nightly temperature, the process turns off the thermostat. Further, if the user is asleep and the lights are on, the process turns off the lights. Similarly, if the user is asleep and the TV is on, the process turns off the TV.

Smart Home

Figure 11:
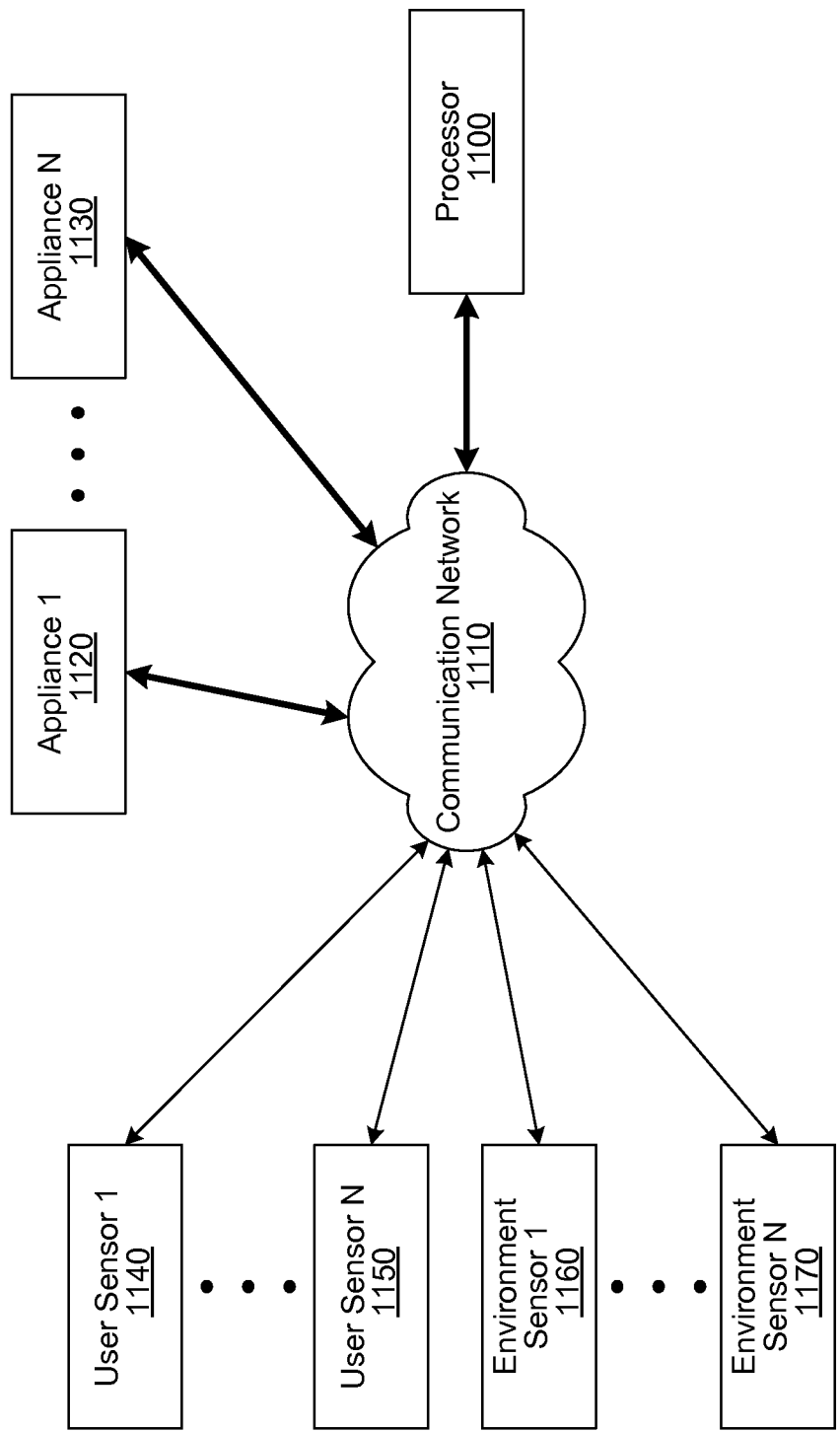
FIG. 11 is a diagram of a system capable of automating the control of the home appliances, according to one embodiment.

FIG. 11 is a diagram of a system capable of automating the control of the home appliances, according to one embodiment. Any number of user sensors 1140, 1150 monitor biological signals associated with said user, such as temperature, motion, presence, heart rate, or breathing rate. Any number of environment sensors 1160, 1170 monitor environment properties, such as temperature, sound, light, or humidity. According to one embodiment, the environment sensors 1160, 1170 are placed next to a bed. The user sensors 1140, 1150 and the environment sensors 1160, 1170 communicate their measurements to the processor 1100. The processor 1100 determines, based on the current biological signals associated with said user, historical biological signals associated with said user, user-specified preferences, exercise data associated with said user, and the environment properties received, a control signal, and a time to send said control signal to an appliance 1120, 1130.

The processor 1100 is any type of microcontroller, or any processor in a mobile terminal, fixed terminal, or portable terminal including a mobile handset, station, unit, device, multimedia computer, multimedia tablet, Internet node, cloud computer, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, the accessories and peripherals of these devices, or any combination thereof.

The processor 1100 can be connected to the user sensor 1140, 1150, or the environment sensor 1160, 1170 by a computer bus, such as an I2C bus. Also, the processor 1100 can be connected to the user sensor 1140, 1150, or environment sensor 1160, 1170 by a communication network 1110. By way of example, the communication network 1110 connecting the processor 1100 to the user sensor 1140, 1150, or the environment sensor 1160, 1170 includes one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

Figure 12:
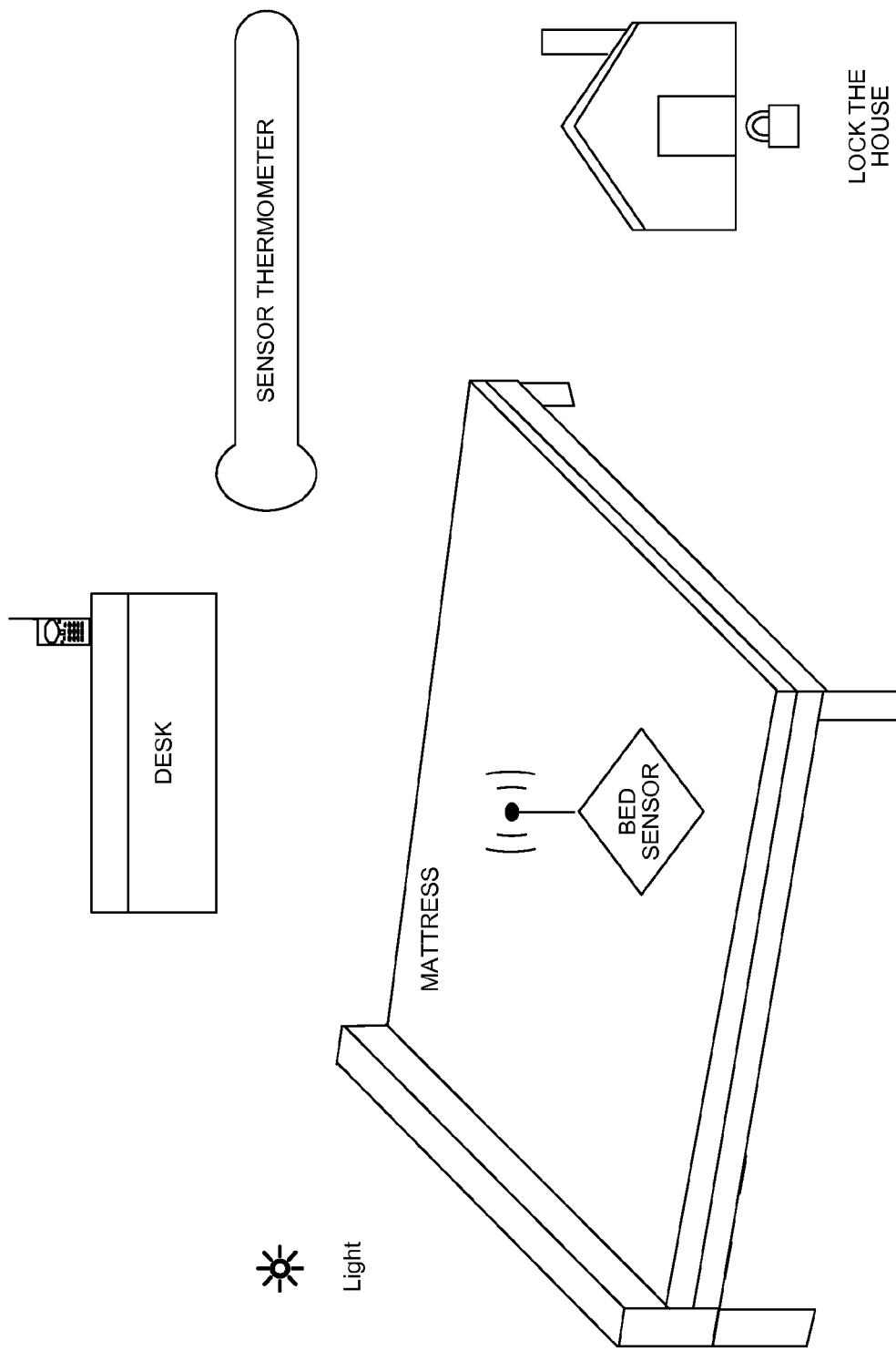
FIG. 12 is an illustration of the system capable of controlling an appliance and a home, according to one embodiment.

FIG. 12 is an illustration of the system capable of controlling an appliance and a home, according to one embodiment. The appliances, that the system disclosed here can control, comprise an alarm, a coffee machine, a lock, a thermostat, a bed device, a humidifier, or a light. For example, the system detects that the user has fallen asleep, the system sends a control signal to the lights to turn off, to the locks to engage, and to the thermostat to lower the temperature. According to another example, if the system detects that the user has woken up and it is morning, the system sends a control signal to the coffee machine to start making coffee.

Figure 13:
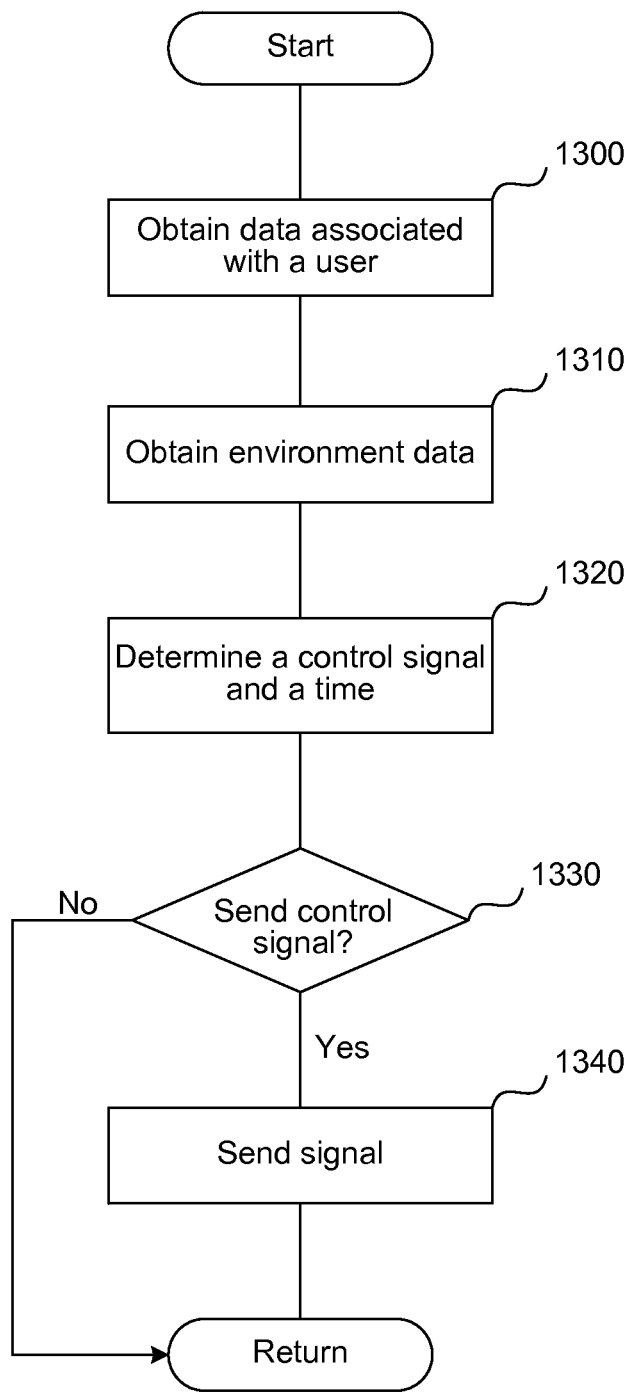
FIG. 13 is a flowchart of the process for controlling an appliance, according to one embodiment.

FIG. 13 is a flowchart of the process for controlling an appliance, according to one embodiment. In one embodiment, at block 1300, the process obtains history of biological signals, such as at what time does the user go to bed on a particular day of the week (e.g. the average bedtime associated with said user on Monday, the average bedtime associated with said user on Tuesday etc.). The history of biological signals can be stored in a database associated with the user, or in a database associated with the bed device. In another embodiment, at block 1300, the process also obtains user specified preferences, such as the preferred bed temperature associated with said user. Based on the history of biological signals and user-specified preferences, the process, at block 1320, determines a control signal, and a time to send said control signal to an appliance. It block 1330, the process determines whether to send a control signal to an appliance. For example, if the current time is within half an hour of average bedtime associated with said user on that particular day of the week, the process, at block 1340, sends a control signal to an appliance. For example, the control signal comprises an instruction to turn on the bed device, and the user specified bed temperature. Alternatively, the bed temperature is determined automatically, such as by calculating the average nightly bed temperature associated with a user.

According to another embodiment, at block 1300, the process obtains a current biological signal associated with a user from a sensor associated with said user. At block 1310, the process also obtains environment data, such as the ambient light, from an environment sensor associated with a bed device. Based on the current biological signal, the process identifies whether the user is asleep. If the user is asleep and the lights are on, the process sends an instruction to turn off the lights. In another embodiment, if the user is asleep, the lights are off, and the ambient light is high, the process sends an instruction to the blinds to shut. In another embodiment, if the user is asleep, the process sends an instruction to the locks to engage.

In another embodiment, the process, at block 1300, obtains history of biological signals, such as at what time the user goes to bed on a particular day of the week (e.g. the average bedtime associated with said user on Monday, the average bedtime associated with said user on Tuesday etc.). The history of biological signals can be stored in a database associated with the bed device, or in a database associated with a user. Alternatively, the user may specify a bedtime for the user for each day of the week. Further, the process obtains the exercise data associated with said user, such as the number of hours the user spent exercising, or the heart rate associated with said user during exercising. According to one embodiment, the process obtains the exercise data from a user phone, a wearable device, fitbit bracelet, or a database associated with said user. Based on the average bedtime for that day of the week, and the exercise data during the day, the process, at block 1320, determines the expected bedtime associated with said user that night. The process then sends an instruction to the bed device to heat to a desired temperature, before the expected bedtime. The desired temperature can be specified by the user, or can be determined automatically, based on the average nightly temperature associated with said user.

Figure 14:
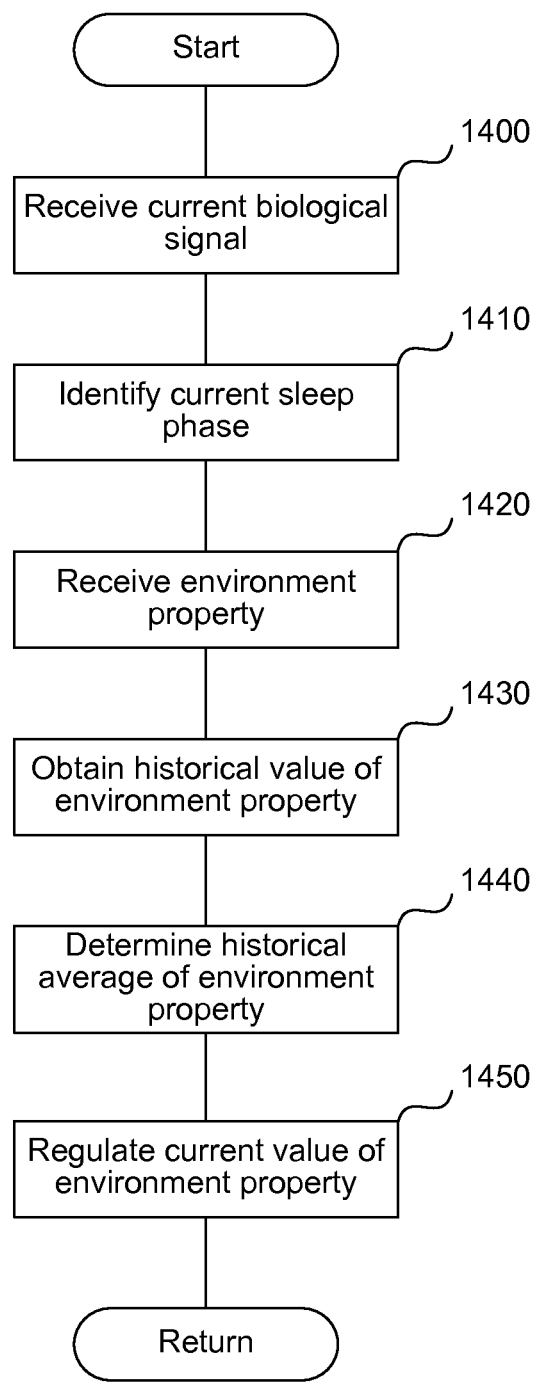
FIG. 14 is a flowchart of the process for controlling an appliance, according to another embodiment.

FIG. 14 is a flowchart of the process for controlling an appliance, according to another embodiment. The process, at block 1400, receives current biological signal associated with said user, such as the heart rate, breathing rate, presence, motion, or temperature, associated with said user. Based on the current biological signal, the process, at block 1410, identifies current sleep phase, such as light sleep, deep sleep, or REM sleep. The process, at block 1420 also receives a current environment property value, such as the temperature, the humidity, the light, or the sound. The process, at block 1430, accesses a database, which stores historical values associated with the environment property and the current sleep phase. That is, the database associates each sleep phase with an average historical value of the different environment properties. The database maybe associated with the bed device, maybe associated with the user, or maybe associated with a remote server. The process, at block 1440, then calculates a new average of the environment property based on the current value of the environment property and the historical value of the environment property, and assigns the new average to the current sleep phase in the database. If there is a mismatch between the current value of the environment property, and the historical average, the process, at block 1450, regulates the current value to match the historical average. For example, the environment property can be the temperature associated with the bed device. The database stores the average bed temperature corresponding to each of the sleep phase, light sleep, deep sleep, REM sleep. If the current bed temperature is below the historical average, the process sends a control signal to increase the temperature of the bed to match the historical average.

Monitoring of Biological Signals

Biological signals associated with a person, such as a heart rate or a breathing rate, indicate said person's state of health. Changes in the biological signals can indicate an immediate onset of a disease, or a long-term trend that increases the risk of a disease associated with said person. Monitoring the biological signals for such changes can predict the onset of a disease, can enable calling for help when the onset of the disease is immediate, or can provide advice to the person if the person is exposed to a higher risk of the disease in the long-term.

Figure 15:
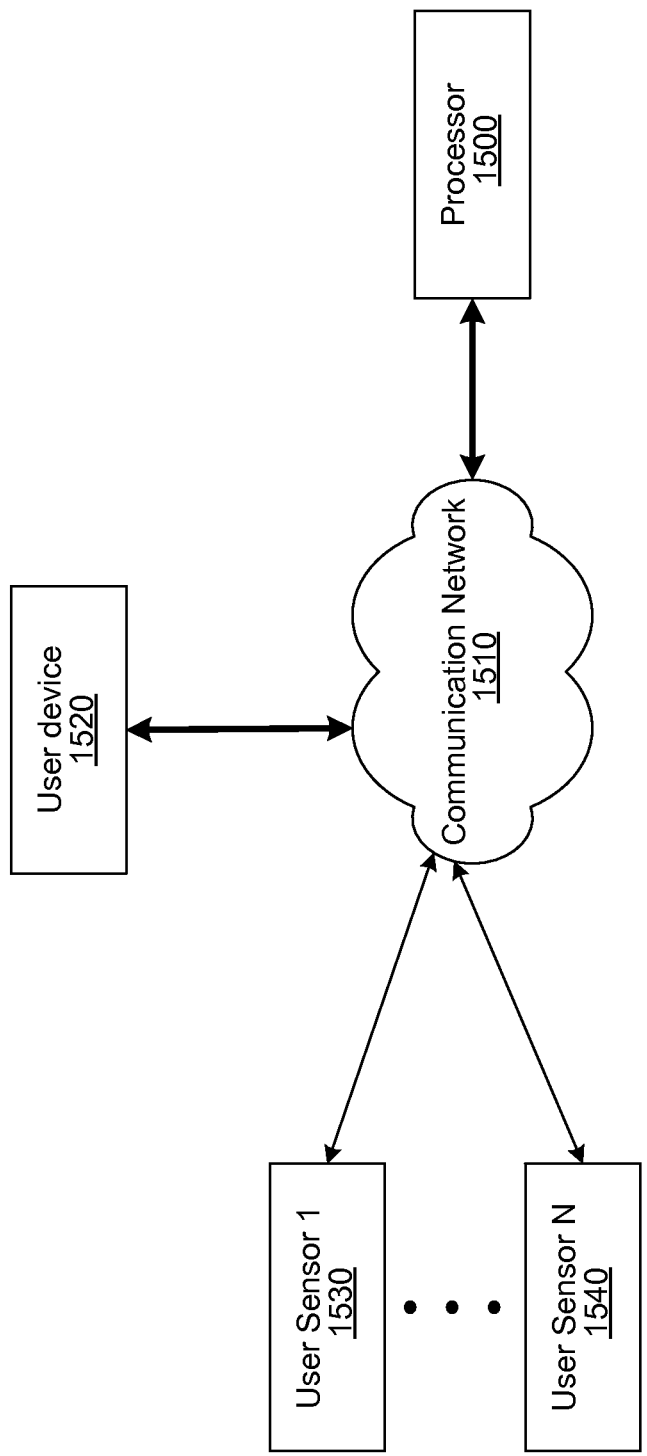
FIG. 15 is a diagram of a system for monitoring biological signals associated with a user, and providing notifications or alarms, according to one embodiment.

FIG. 15 is a diagram of a system for monitoring biological signals associated with a user, and providing notifications or alarms, according to one embodiment. Any number of user sensors 1530, 1540 monitor bio signals associated with said user, such as temperature, motion, presence, heart rate, or breathing rate. The user sensors 1530, 1540 communicate their measurements to the processor 1500. The processor 1500 determines, based on the bio signals associated with said user, historical biological signals associated with said user, or user-specified preferences whether to send a notification or an alarm to a user device 1520. In some embodiments, the user device 1520 and the processor 1500 can be the same device.

The user device 1520 is any type of a mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, the accessories and peripherals of these devices, or any combination thereof.

The processor 1500 is any type of microcontroller, or any processor in a mobile terminal, fixed terminal, or portable terminal including a mobile handset, station, unit, device, multimedia computer, multimedia tablet, Internet node, cloud computer, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, the accessories and peripherals of these devices, or any combination thereof.

The processor 1500 can be connected to the user sensor 1530, 1540 by a computer bus, such as an I2C bus. Also, the processor 1500 can be connected to the user sensor 1530, 1540 by a communication network 1510. By way of example, the communication network 1510 connecting the processor 1500 to the user sensor 1530, 1540 includes one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

Figure 16:
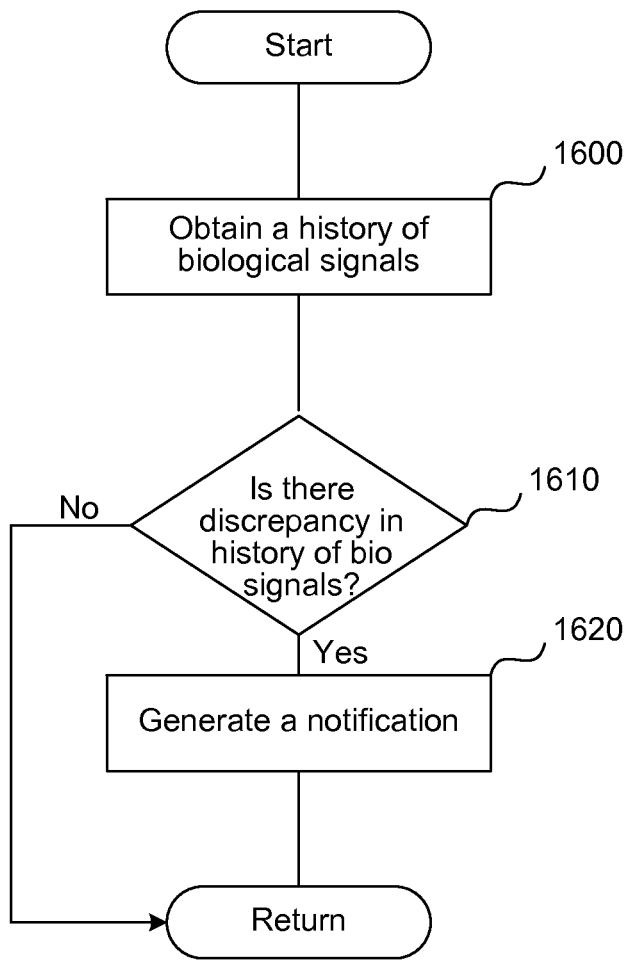
FIG. 16 is a flowchart of a process for generating a notification based on a history of biological signals associated with a user, according to one embodiment.

FIG. 16 is a flowchart of a process for generating a notification based on a history of biological signals associated with a user, according to one embodiment. The process, at block 1600, obtains a history of biological signals, such as the presence history, motion history, breathing rate history, or heart rate history, associated with said user. The history of biological signals can be stored in a database associated with a user. At block 1610, the process determines if there is an irregularity in the history of biological signals within a timeframe. If there is an irregularity, at block 1620, the process generates a notification to the user. The timeframe can be specified by the user, or can be automatically determined based on the type of irregularity. For example, the heart rate associated with said user goes up within a one day timeframe when the user is sick. According to one embodiment, the process detects an irregularity, specifically, that a daily heart rate associated with said user is higher than normal. Consequently, the process warns the user that the user may be getting sick. According to another embodiment, the process detects an irregularity, such as that an elderly user is spending at least 10% more time in bed per day over the last several days, than the historical average. The process generates a notification to the elderly user, or to the elderly user's caretaker, such as how much more time the elderly user is spending in bed. In another embodiment, the process detects an irregularity such as an increase in resting heart rate, by more than 15 beats per minute, over a ten-year period. Such an increase in the resting heart rate doubles the likelihood that the user will die from a heart disease, compared to those people whose heart rates remained stable. Consequently, the process warns the user that the user is at risk of a heart disease.

Figure 17:
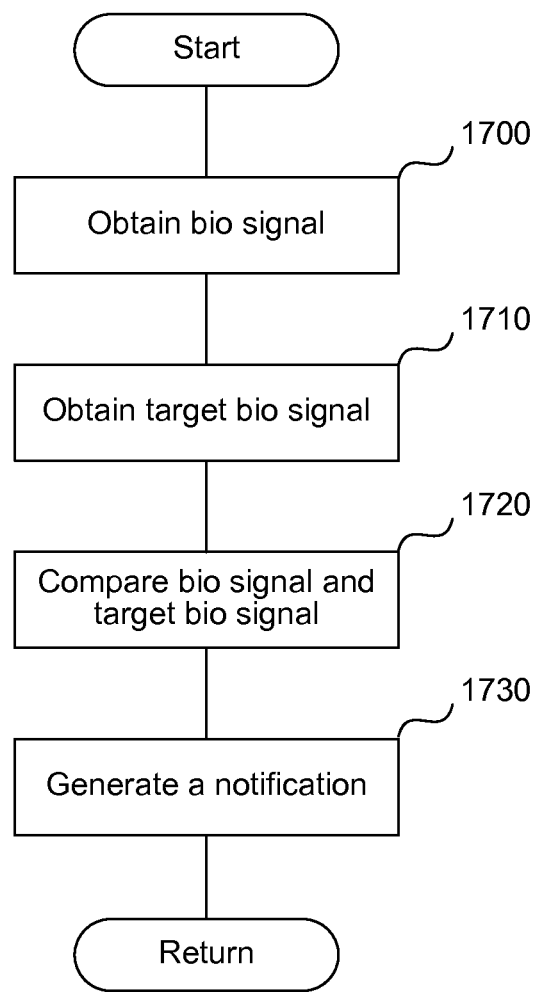
FIG. 17 is a flowchart of a process for generating a comparison between a biological signal associated with a user and a target biological signal, according to one embodiment.

FIG. 17 is a flowchart of a process for generating a comparison between a biological signal associated with a user and a target biological signal, according to one embodiment. The process, at block 1700, obtains a current biological signal associated with a user, such as presence, motion, breathing rate, temperature, or heart rate, associated with said user. The process obtains said current biological signal from a sensor associated with said user. The process, at block 1710, then obtains a target biological signal, such as a user-specified biological signal, a biological signal associated with a healthy user, or a biological signal associated with an athlete. According to one embodiment, the process obtains said target biological signal from a user, or a database storing biological signals. The process, at block 1720, compares current bio signal associated with said user and target bio signal, and generates a notification based on the comparison 1730. The comparison of the current bio signal associated with said user and target bio signal comprises detecting a higher frequency in the current biological signal then in the target biological signal, detecting a lower frequency in the current biological signal than in the target biological signal, detecting higher amplitude in the current biological signal than in the target biological signal, or detecting lower amplitude in the current biological signal than in the target biological signal.

According to one embodiment, the process of FIG. 17 can be used to detect if an infant has a higher risk of sudden infant death syndrome ("SIDS"). In SIDS victims less than one month of age, heart rate is higher than in healthy infants of same age, during all sleep phases. SIDS victims greater than one month of age show higher heart rates during REM sleep phase. In case of monitoring an infant for a risk of SIDS, the process obtains the current bio signal associated with the sleeping infant, and a target biological signal associated with the heart rate of a healthy infant, where the heart rate is at the high end of a healthy heart rate spectrum. The process obtains the current bio signal from a user sensor associated with the sleeping infant. The process obtains said target biological signal from a database of biological signals. If the frequency of the biological signal of the infant exceeds the target biological signal, the process generates a notification to the infant's caretaker, that the infant is at higher risk of SIDS.

According to another embodiment, the process of FIG. 17 can be used in fitness training. A normal resting heart rate for adults ranges from 60 to 100 beats per minute. Generally, a lower heart rate at rest implies more efficient heart function and better cardiovascular fitness. For example, a well-trained athlete might have a normal resting heart rate closer to 40 beats per minute. Thus, a user may specify a target rest heart rate of 40 beats per minute. The process FIG. 17 generates a comparison between the actual bio signal associated with said user and the target bio signal 1720, and based on the comparison, the process generates a notification whether the user has reached his target, or whether the user needs to exercise more 1730.

Figure 18:
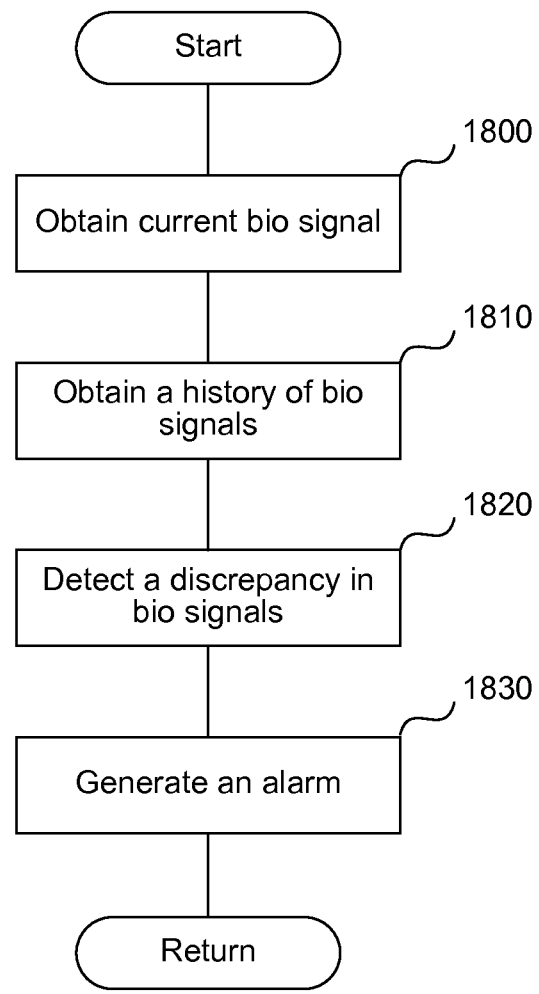
FIG. 18 is a flowchart of a process for detecting the onset of a disease, according to one embodiment.

FIG. 18 is a flowchart of a process for detecting the onset of a disease, according to one embodiment. The process, at block 1800, obtains the current bio signal associated with a user, such as presence, motion, temperature, breathing rate, or heart rate, associated with said user. The process obtains the current bio signal from a sensor associated with said user. Further, the process, at block 1810, obtains a history of bio signals associated with said user from a database. The history of bio signals comprises the bio signals associated with said user, accumulated over time. The history of biological signals can be stored in a database associated with a user. The process, at block 1820, then detects a discrepancy between the current bio signal and the history of bio signals, where the discrepancy is indicative of an onset of a disease. The process, at block 1830, then generates an alarm to the user's caretaker. The discrepancy between the current bio signal and the history of bio signals comprises a higher frequency in the current bio signal than in the history of bio signals, or a lower frequency in the current bio signal than in the history of bio signals.

According to one embodiment, the process of FIG. 18 can be used to detect an onset of an epileptic seizure. A healthy person has a normal heart rate between 60 and 100 beats per minute. During epileptic seizures, the median heart rate associated with said person exceeds 100 beats per minute. The process of FIG. 18 detects that the heart rate associated with said user exceeds the normal heart rate range associated with said user. The process then generates an alarm to the user's caretaker that the user is having an epileptic seizure. Although rare, epileptic seizures can cause the median heart rate associated with a person to drop below 40 beats per minute. Similarly, the process of FIG. 18 detects if the current heart rate is below the normal heart rate range associated with said user. The process then generates an alarm to the user's caretaker that the user is having an epileptic seizure.

Figure 19:
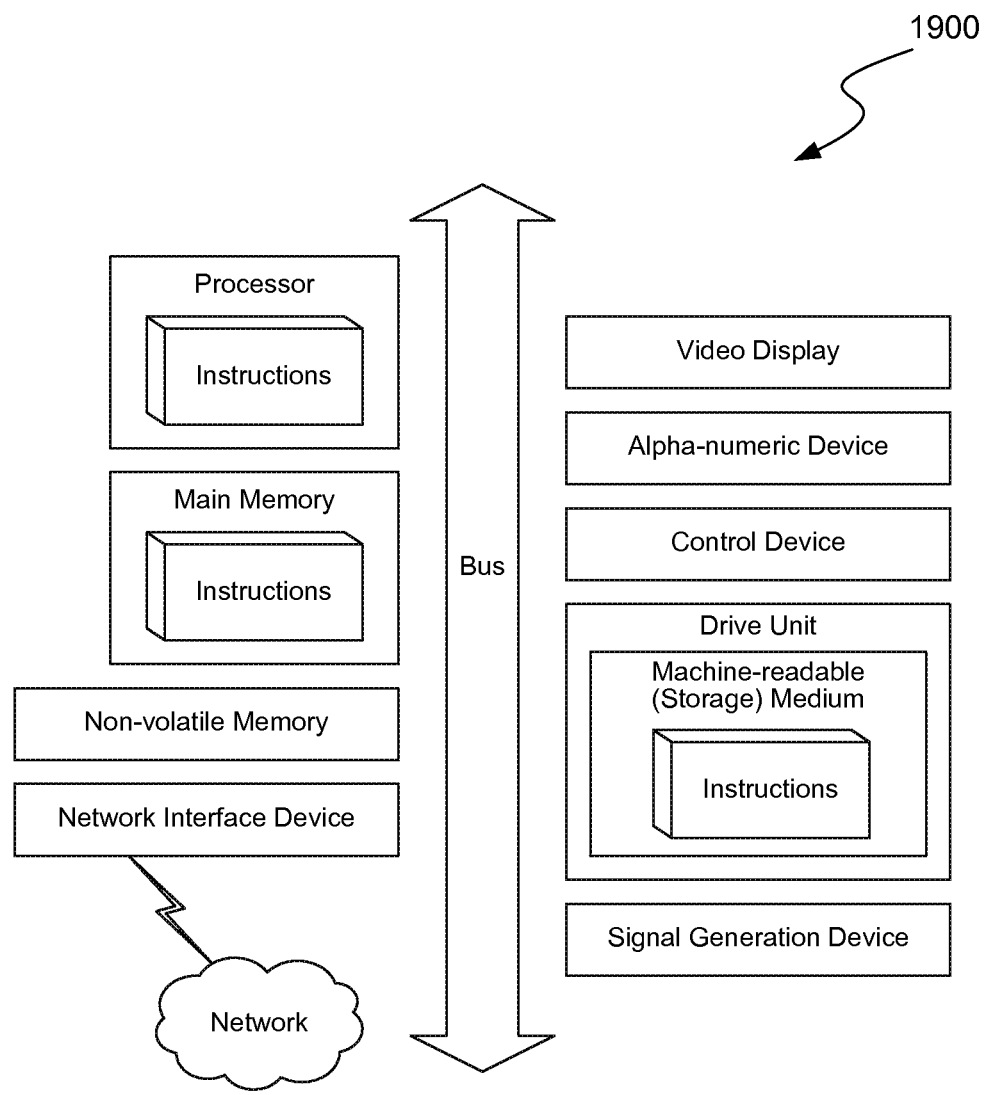
FIG. 19 is a diagrammatic representation of a machine in the example form of a computer system within which a set of instructions, for causing the machine to perform any one or more of the methodologies or modules discussed herein, may be executed.

FIG. 19 is a diagrammatic representation of a machine in the example form of a computer system 1900 within which a set of instructions, for causing the machine to perform any one or more of the methodologies or modules discussed herein, may be executed.

In the example of FIG. 19, the computer system 1900 includes a processor, memory, non-volatile memory, and an interface device. Various common components (e.g., cache memory) are omitted for illustrative simplicity. The computer system 1900 is intended to illustrate a hardware device on which any of the components described in the example of FIGS. 1-18 (and any other components described in this specification) can be implemented. The computer system 1900 can be of any applicable known or convenient type. The components of the computer system 1900 can be coupled together via a bus or through some other known or convenient device.

This disclosure contemplates the computer system 1900 taking any suitable physical form. As example and not by way of limitation, computer system 1900 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, computer system 1900 may include one or more computer systems 1900; be unitary or distributed; span multiple locations; span multiple machines; or reside in a cloud, which may include one or more cloud components in one or more networks. Where appropriate, one or more computer systems 1900 may perform without substantial spatial or temporal limitation one or more steps of one or more methods described or illustrated herein. As an example and not by way of limitation, one or more computer systems 1900 may perform in real time or in batch mode one or more steps of one or more methods described or illustrated herein. One or more computer systems 1900 may perform at different times or at different locations one or more steps of one or more methods described or illustrated herein, where appropriate.

The processor may be, for example, a conventional microprocessor such as an Intel Pentium microprocessor or Motorola power PC microprocessor. One of skill in the relevant art will recognize that the terms "machine-readable (storage) medium" or "computer-readable (storage) medium" include any type of device that is accessible by the processor.

The memory is coupled to the processor by, for example, a bus. The memory can include, by way of example but not limitation, random access memory (RAM), such as dynamic RAM (DRAM) and static RAM (SRAM). The memory can be local, remote, or distributed.

The bus also couples the processor to the non-volatile memory and drive unit. The non-volatile memory is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software in the computer 1900. The non-volatile storage can be local, remote, or distributed. The non-volatile memory is optional because systems can be created with all applicable data available in memory. A typical computer system will usually include at least a processor, memory, and a device (e.g., a bus) coupling the memory to the processor.

Software is typically stored in the non-volatile memory and/or the drive unit. Indeed, storing and entire large program in memory may not even be possible. Nevertheless, it should be understood that for software to run, if necessary, it is moved to a computer readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable medium." A processor is considered to be "configured to execute a program" when at least one value associated with the program is stored in a register readable by the processor.

The bus also couples the processor to the network interface device. The interface can include one or more of a modem or network interface. It will be appreciated that a modem or network interface can be considered to be part of the computer system 1900. The interface can include an analog modem, isdn modem, cable modem, token ring interface, satellite transmission interface (e.g. "direct PC"), or other interfaces for coupling a computer system to other computer systems. The interface can include one or more input and/or output devices. The I/O devices can include, by way of example but not limitation, a keyboard, a mouse or other pointing device, disk drives, printers, a scanner, and other input and/or output devices, including a display device. The display device can include, by way of example but not limitation, a cathode ray tube (CRT), liquid crystal display (LCD), or some other applicable known or convenient display device. For simplicity, it is assumed that controllers of any devices not depicted in the example of FIG. 9 reside in the interface.

In operation, the computer system 1900 can be controlled by operating system software that includes a file management system, such as a disk operating system. One example of operating system software with associated file management system software is the family of operating systems known as Windows® from Microsoft Corporation of Redmond, Wash., and their associated file management systems. Another example of operating system software with its associated file management system software is the Linux™ operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "generating" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may thus be implemented using a variety of programming languages.

In alternative embodiments, the machine operates as a standalone device or may be connected (e.g., networked) to other machines. In a networked deployment, the machine may operate in the capacity of a server or a client machine in a client-server network environment, or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies or modules of the presently disclosed technique and innovation.

In general, the routines executed to implement the embodiments of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and storage of charge or a release of stored charge. Likewise, in other memory devices, a change of state may comprise a physical change or transformation in magnetic orientation or a physical change or transformation in molecular structure, such as from crystalline to amorphous or vice versa. The foregoing is not intended to be an exhaustive list of all exam page on ples in which a change in state for a binary one to a binary zero or vice-versa in a memory device may comprise a transformation, such as a physical transformation. Rather, the foregoing is intended as illustrative examples.

A storage medium typically may be non-transitory or comprise a non-transitory device. In this context, a non-transitory storage medium may include a device that is tangible, meaning that the device has a concrete physical form, although the device may change its physical state. Thus, for example, non-transitory refers to a device remaining tangible despite this change in state.

Remarks

In many of the embodiments disclosed in this application, the technology is capable of allowing multiple different users to use the same piece of furniture equipped with the presently disclosed technology. For example, different people can sleep in the same bed. In addition, two different users can switch the side of the bed that they sleep on, and the technology disclosed here will correctly identify which user is sleeping on which side of the bed. The technology identifies the users based on any of the following signals alone or in combination: heart rate, breathing rate, body motion, or body temperature associated with each user.

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling others skilled in the relevant art to understand the claimed subject matter, the various embodiments, and the various modifications that are suited to the particular uses contemplated.

While embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Although the above Detailed Description describes certain embodiments and the best mode contemplated, no matter how detailed the above appears in text, the embodiments can be practiced in many ways. Details of the systems and methods may vary considerably in their implementation details, while still being encompassed by the specification. As noted above, particular terminology used when describing certain features or aspects of various embodiments should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless those terms are explicitly defined herein. Accordingly, the actual scope of the invention encompasses not only the disclosed embodiments, but also all equivalent ways of practicing or implementing the embodiments under the claims.

The language used in the specification has been principally selected for readability and instructional purposes, and it may not have been selected to delineate or circumscribe the inventive subject matter. It is therefore intended that the scope of the invention be limited not by this Detailed Description, but rather by any claims that issue on an application based hereon. Accordingly, the disclosure of various embodiments is intended to be illustrative, but not limiting, of the scope of the embodiments, which is set forth in the following claims.

The invention claimed is:

1. A method comprising:
obtaining a biological signal associated with a user from a sensor, wherein said biological signal corresponds to a heart rate associated with said user, a temperature associated with said user, a motion associated with said user, and breathing rate associated with said user; and
identifying, using a processor, said user based on at least one of: said heart rate associated with said user, said breathing rate associated with said user, said temperature associated with said user, or said motion associated with said user; and
determining a control signal, and a time to send said control signal to a coil, using said processor, wherein said control signal comprises one of an instruction to heat said coil to a high temperature, or an instruction to cool said coil to a low temperature, and further wherein said time comprises an average bedtime associated with said user; and
sending said control signal at said average bedtime associated with said user to said coil, such that said coil is heated or cooled according to said control signal.

2. The method of claim 1, wherein said high temperature comprises an average high temperature associated with said user.

3. The method of claim 1, wherein said low temperature comprises an average low temperature associated with said user.

* * * * *